(12) United States Patent
Kwon

(10) Patent No.: US 12,378,532 B2
(45) Date of Patent: Aug. 5, 2025

(54) FOOD COMPOSITION CONTAINING NOVEL ALDEHYDE DEHYDROGENASE FOR IMPROVING MEMORY AND COGNITIVE FUNCTION

(71) Applicant: PICOENTECH Co., LTD., Seongnam-Si (KR)

(72) Inventor: Hung Taeck Kwon, Seoul (KR)

(73) Assignee: PICOENTECH Co., LTD., Seongnam-Si (KR)

( * ) Notice: Subject to any disclaimer, the term of this patent is extended or adjusted under 35 U.S.C. 154(b) by 0 days.

(21) Appl. No.: 18/935,987

(22) Filed: Nov. 4, 2024

(65) Prior Publication Data
US 2025/0059518 A1 Feb. 20, 2025

Related U.S. Application Data

(63) Continuation of application No. 18/519,546, filed on Nov. 27, 2023.

(30) Foreign Application Priority Data

Dec. 1, 2022 (KR) .......................... 10-2022-0165816
Nov. 7, 2023 (KR) .......................... 10-2023-0153059

(51) Int. Cl.
*A61P 25/28* (2006.01)
*A61K 36/064* (2006.01)
*C12N 1/18* (2006.01)
*C12N 9/02* (2006.01)
*C12R 1/865* (2006.01)

(52) U.S. Cl.
CPC .......... *C12N 9/0008* (2013.01); *A61K 36/064* (2013.01); *A61P 25/28* (2018.01); *C12N 1/18* (2013.01); *C12R 2001/865* (2021.05); *C12Y 102/01003* (2013.01)

(58) Field of Classification Search
CPC . C12N 15/90; C12N 1/18; A61P 25/00; A61P 25/28; C12Y 102/01003; C12Y 102/01005
USPC .......................................... 435/375
See application file for complete search history.

(56) References Cited

U.S. PATENT DOCUMENTS

2024/0191210 A1* 6/2024 Kwon

* cited by examiner

*Primary Examiner* — Robert B Mondesi
*Assistant Examiner* — Mohammad Y Meah
(74) *Attorney, Agent, or Firm* — Maier & Maier, PLLC

(57) ABSTRACT

The compositions contain a novel aldehyde dehydrogenase derived from a novel mutant yeast, that improve memory and cognitive function. The embodiments relate to a food and pharmaceutical composition for preventing Alzheimer's disease and Huntington disease by reducing the accumulation of lesional proteins in brain tissue. The food or pharmaceutical compositions contain a lysate of any one or a mixture thereof selected from *Saccharomyces cerevisiae*, KCTC13925BP, KCTC14122BP, KCTC14123BP, KCTC14983BP, KCTC14984BP and KCTC14985BP.

6 Claims, 15 Drawing Sheets

Specification includes a Sequence Listing.

[Figure 1]
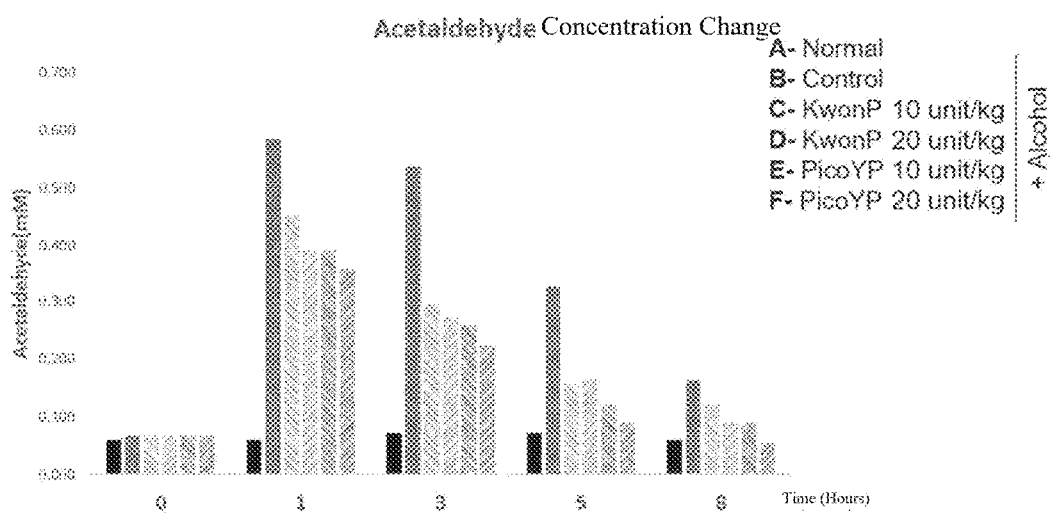
[Figure 2]
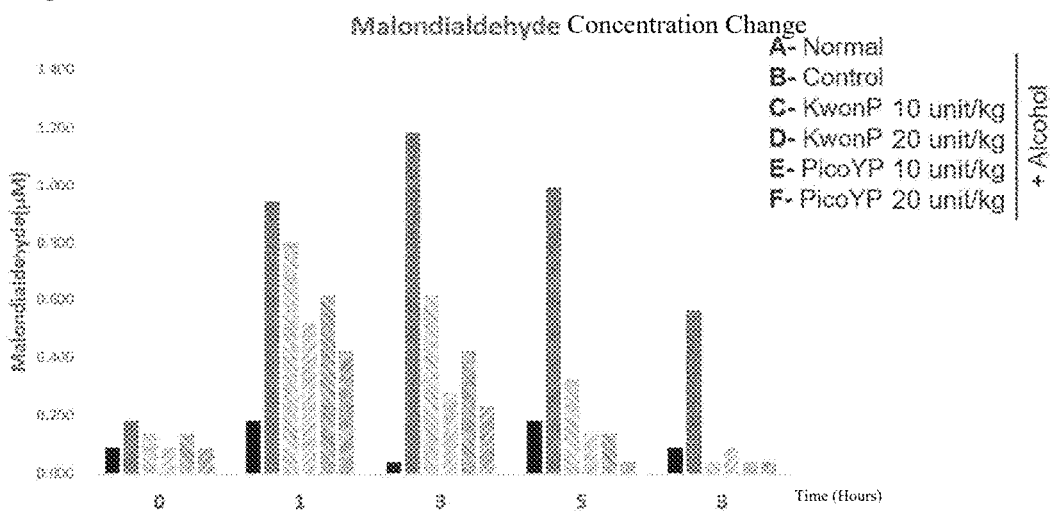

[Figure 3]
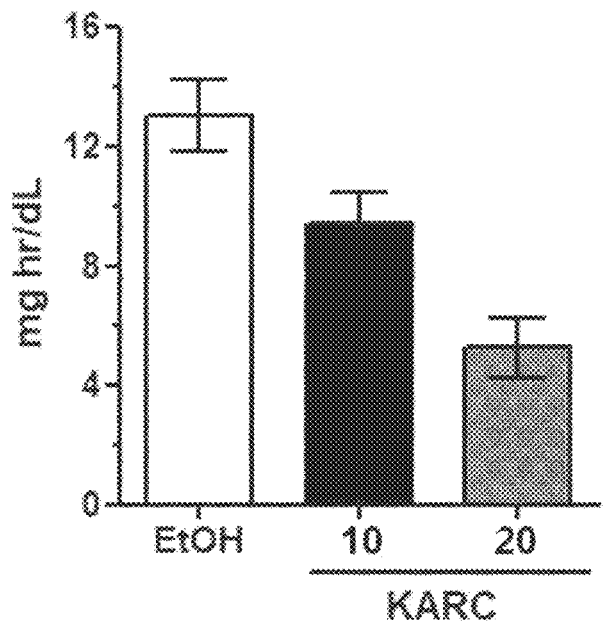
[Figure 4]
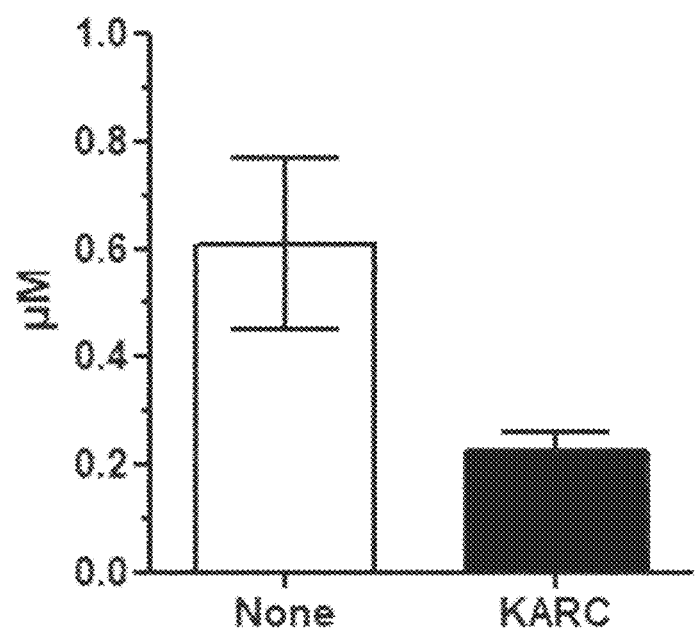

[Figure 5]
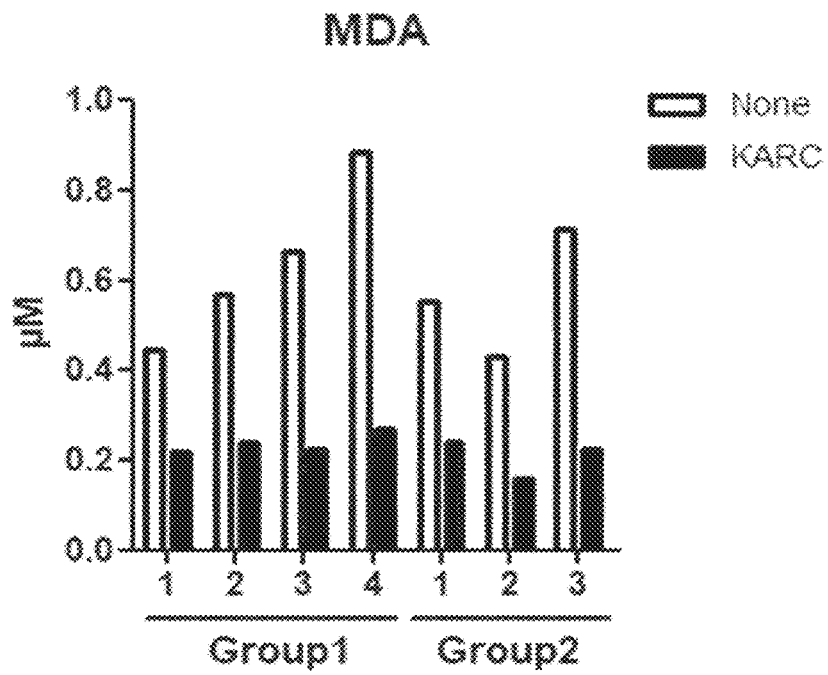
[Figure 6]
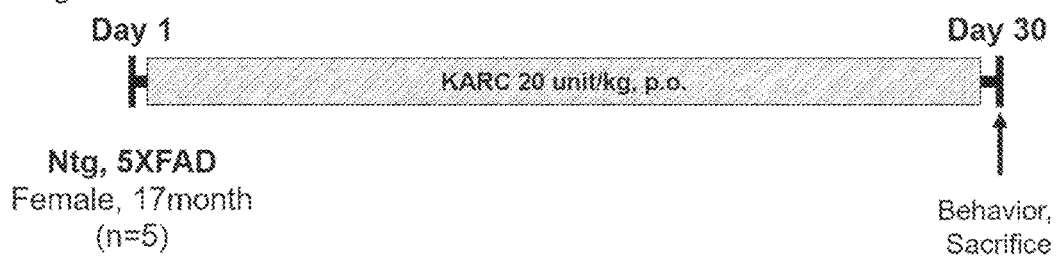
Day 1
Ntg, 5XFAD
Female, 17month
(n=5)
Day 30
Behavior,
Sacrifice

[Figure 7]
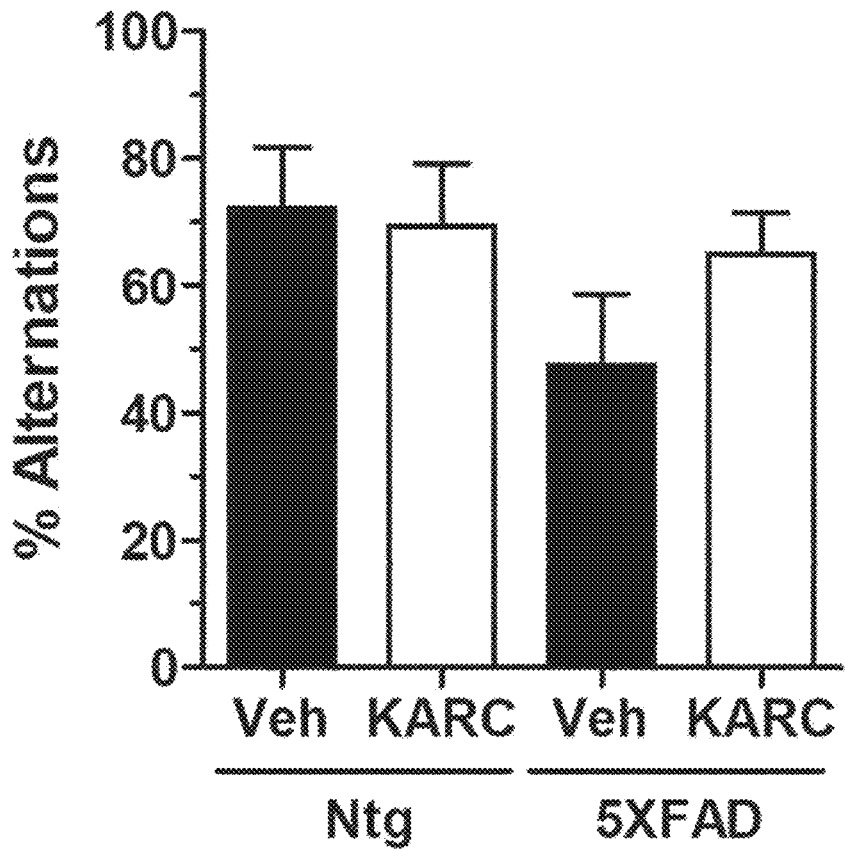
[Figure 8]
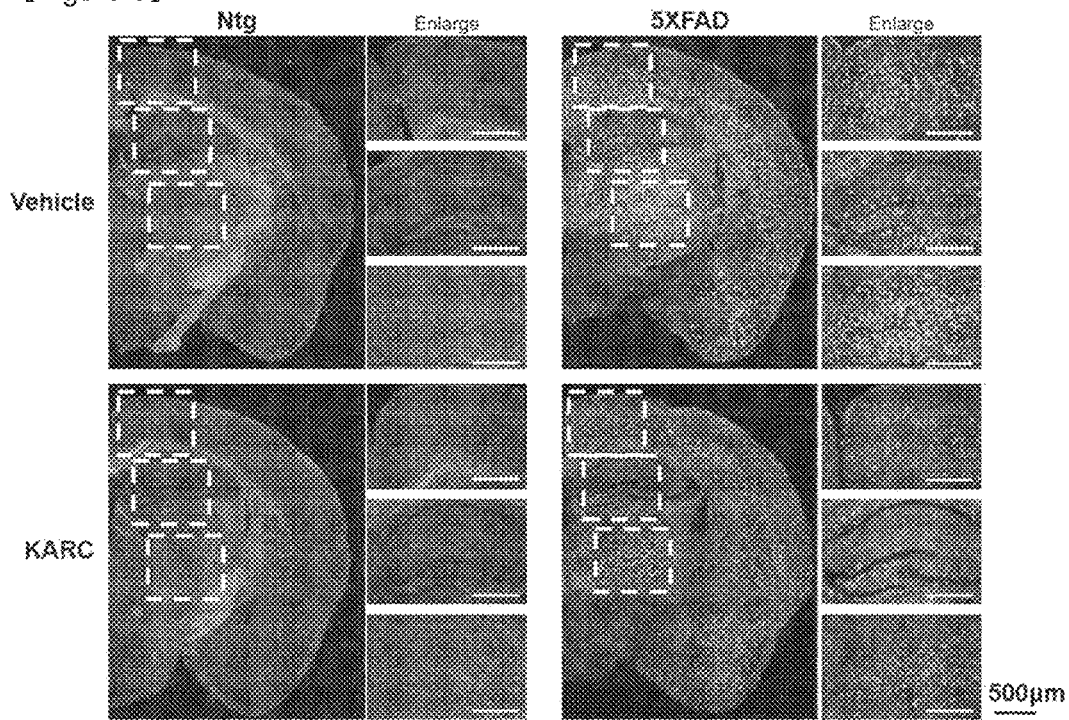

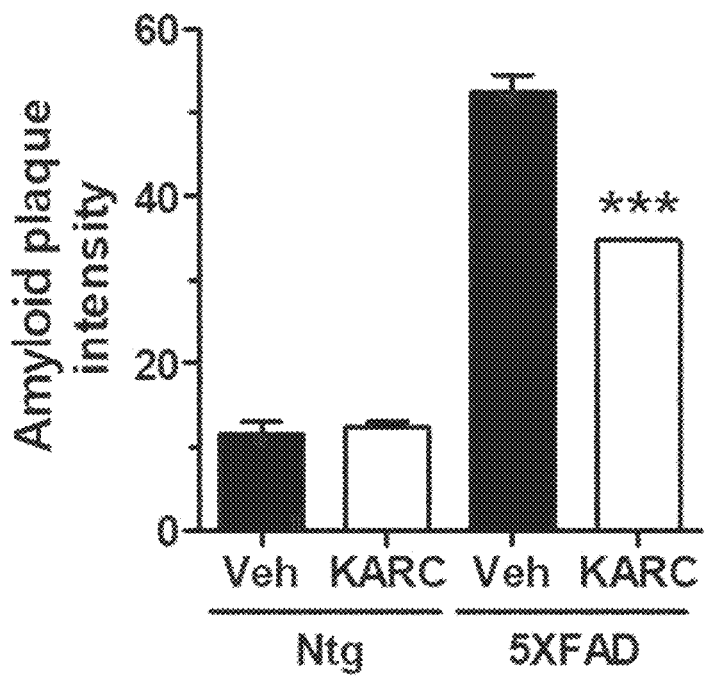
[Figure 9]
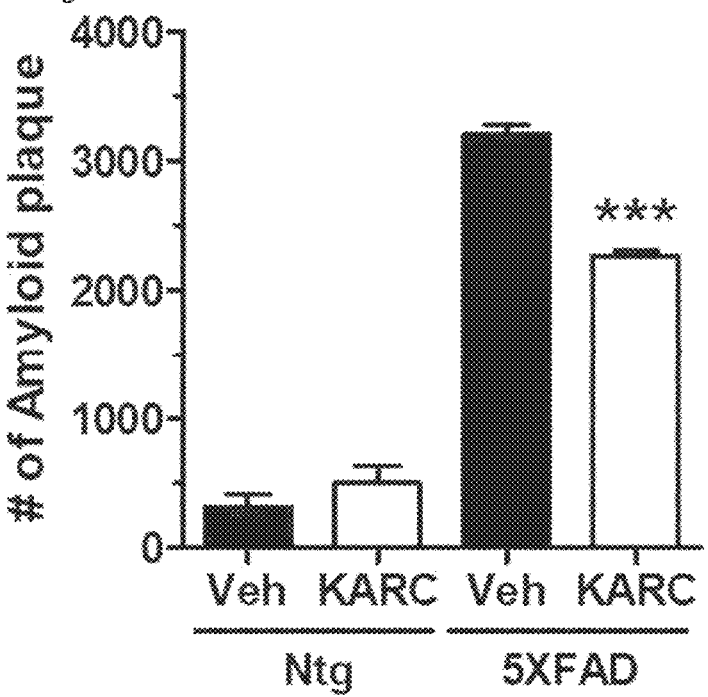
[Figure 10]

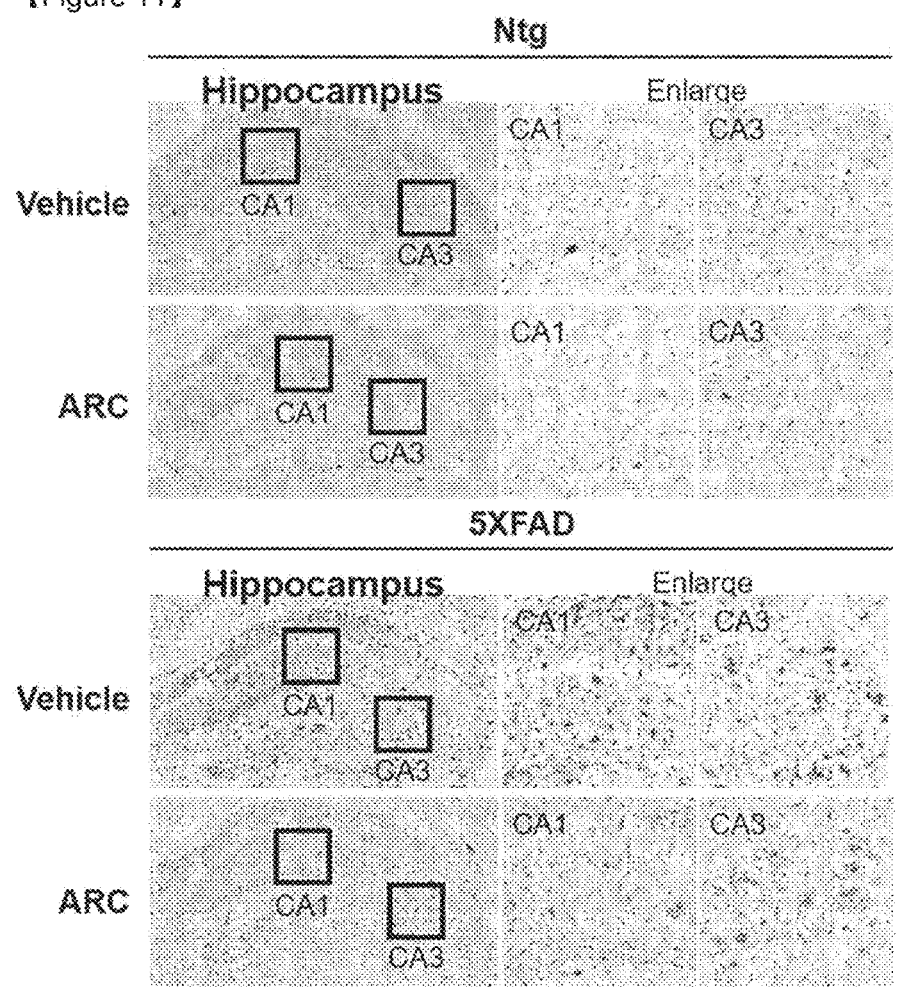
[Figure 11]

[Figure 12]
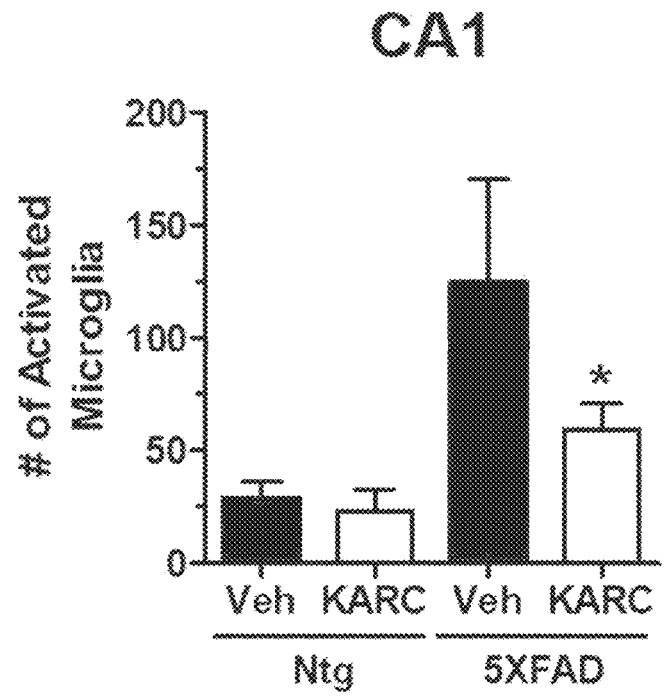
[Figure 13]
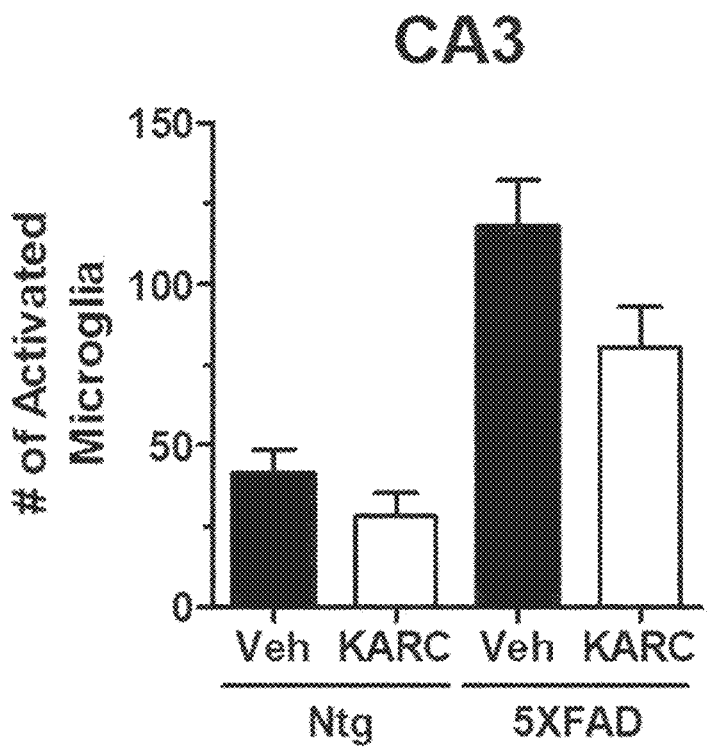

[Figure 14]
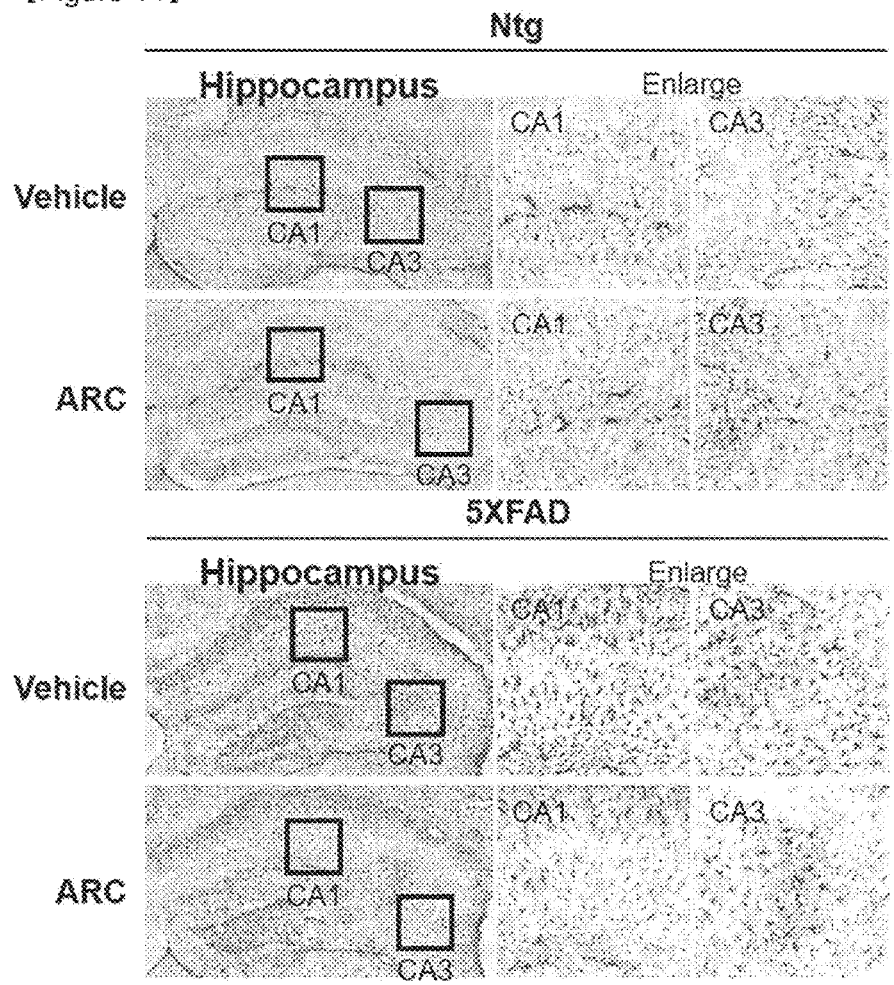

[Figure 15]
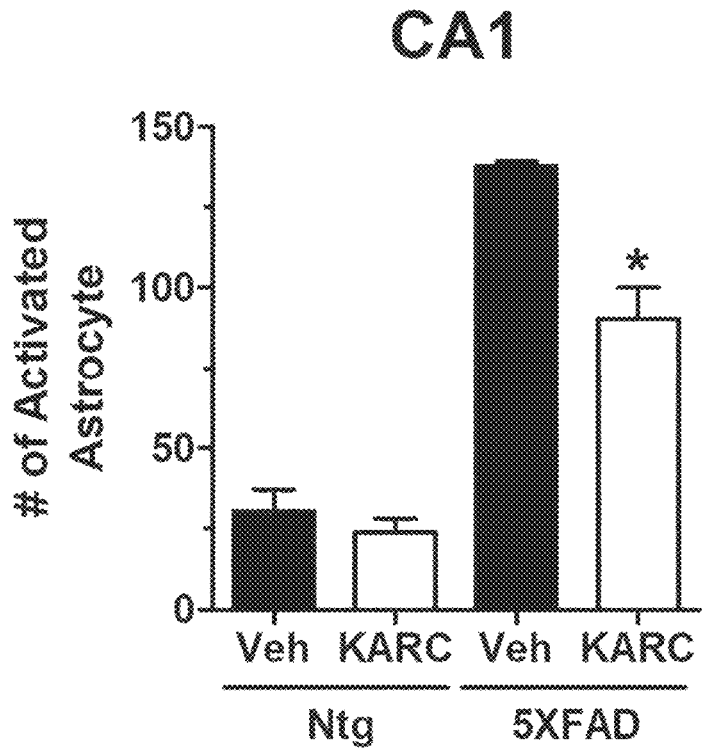
[Figure 16]
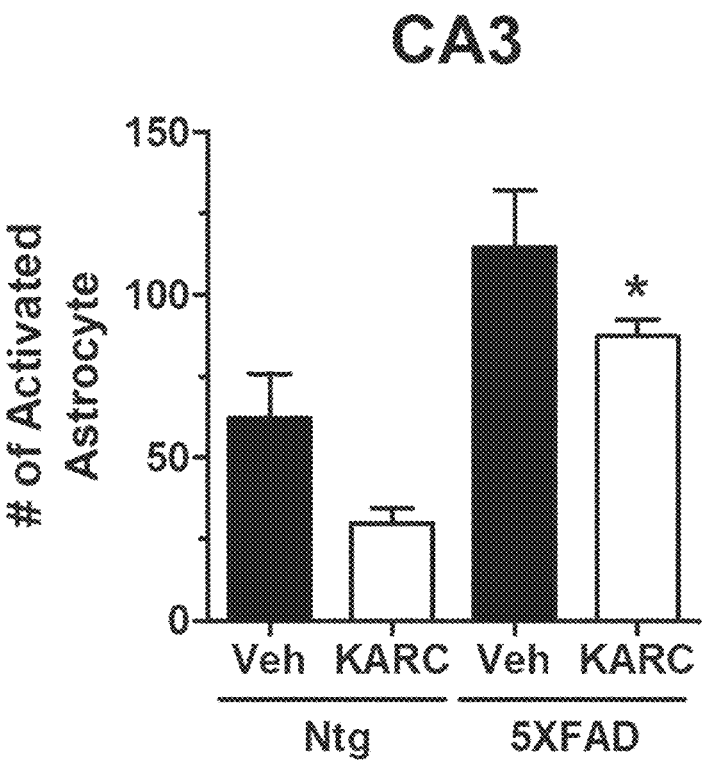

[Figure 17]
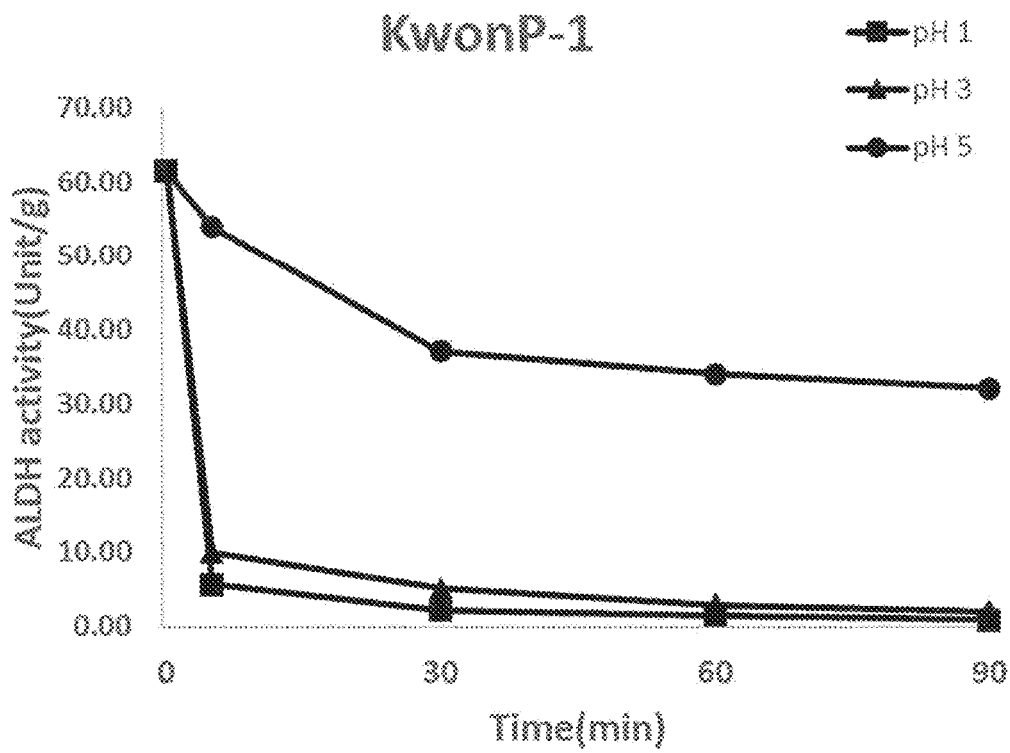
[Figure 18]
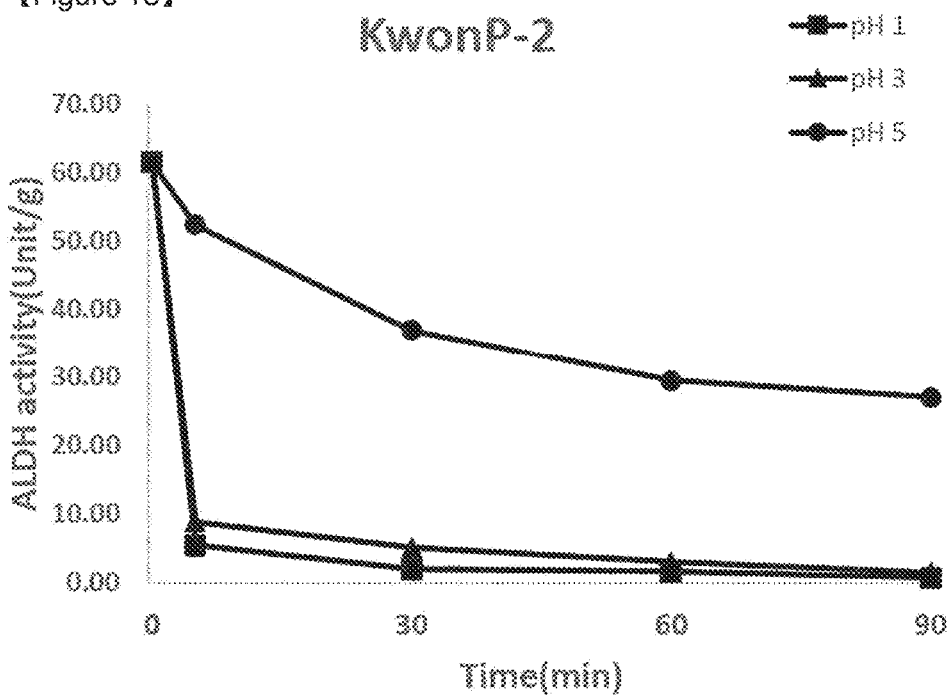

[Figure 19]
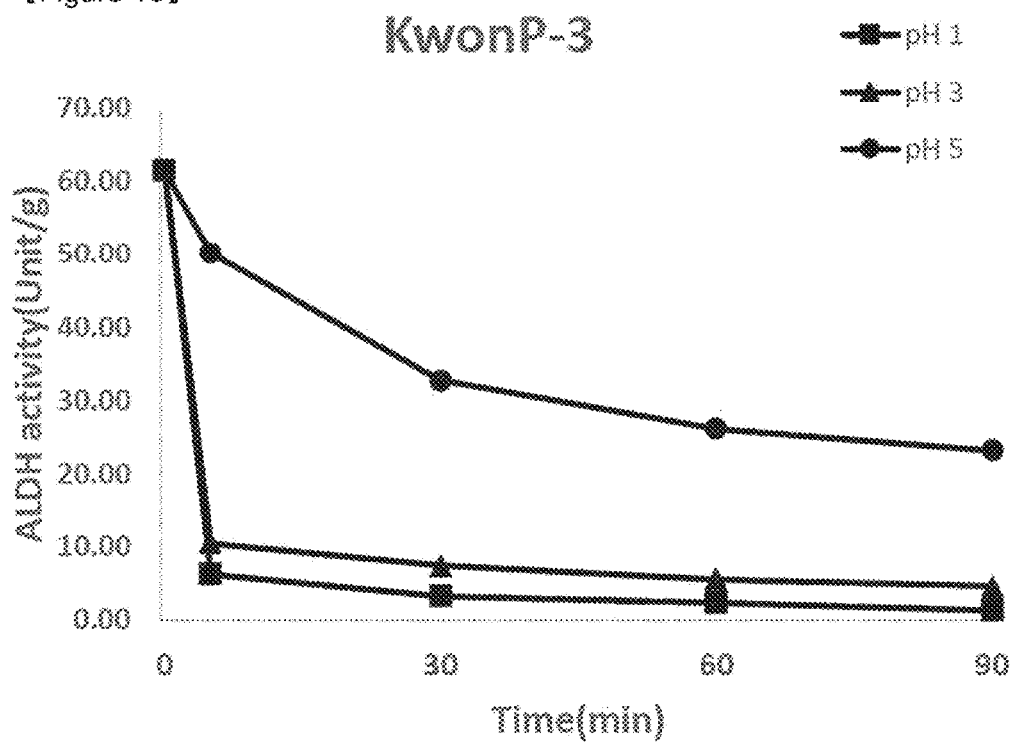
[Figure 20]
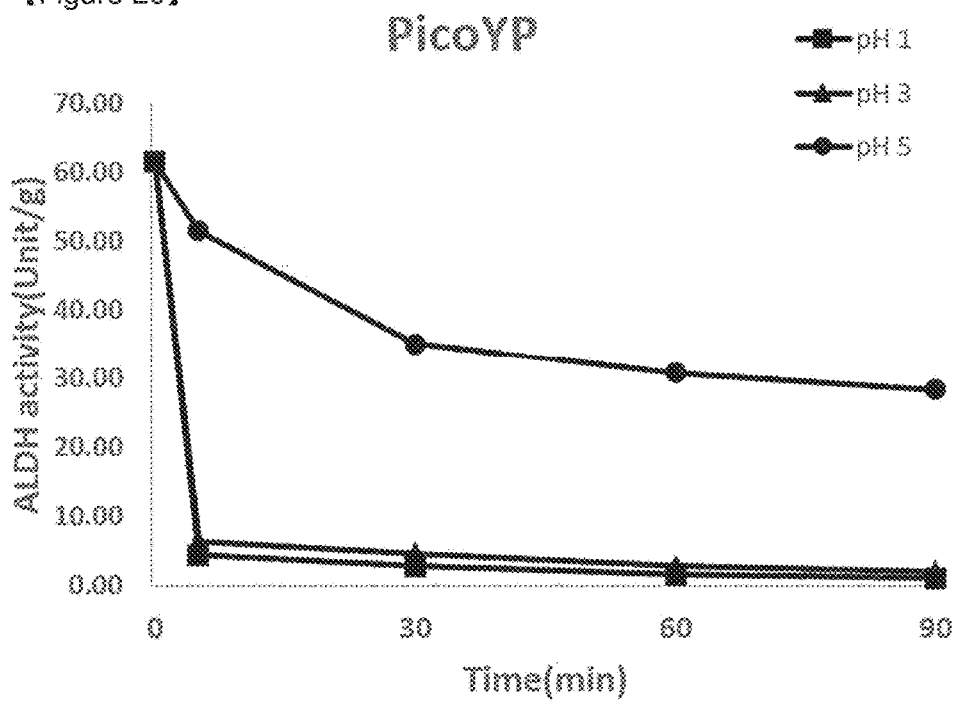

[Figure 21]
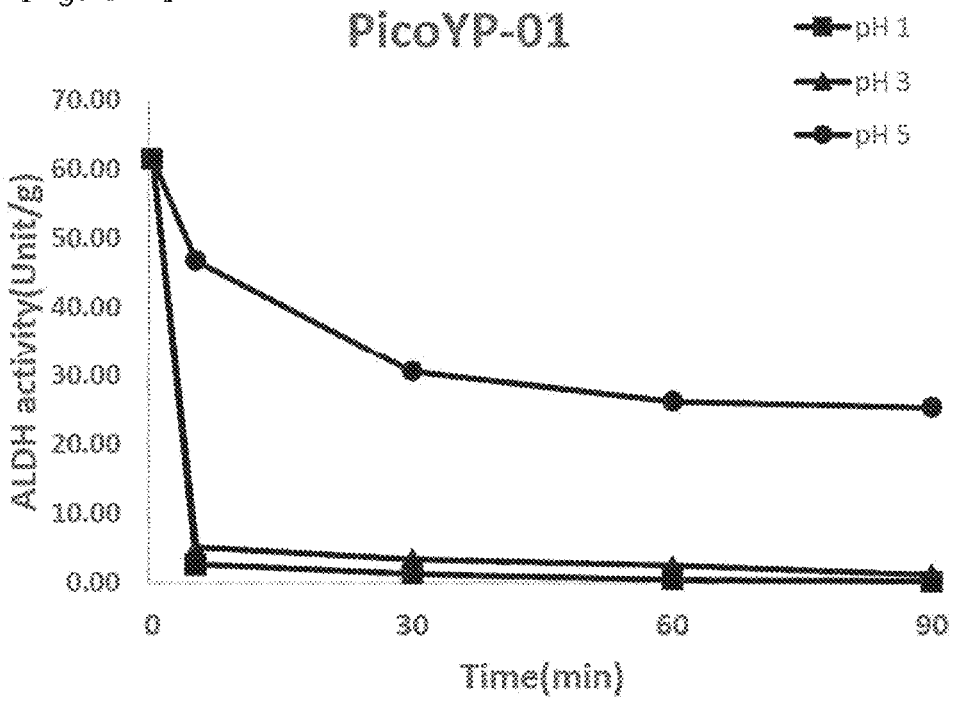
[Figure 22]
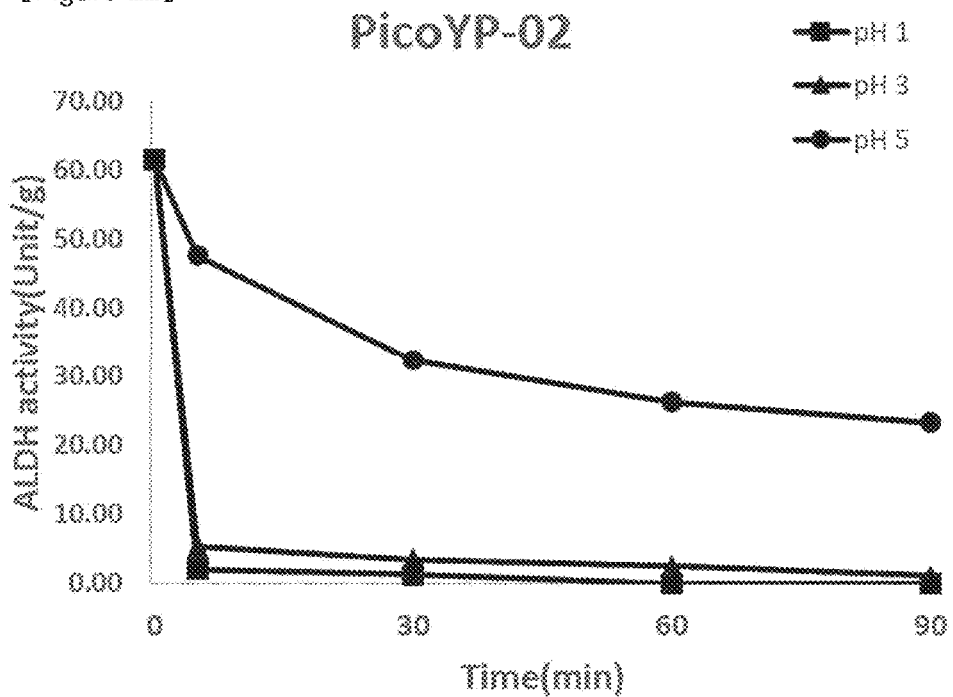

[Figure 23]
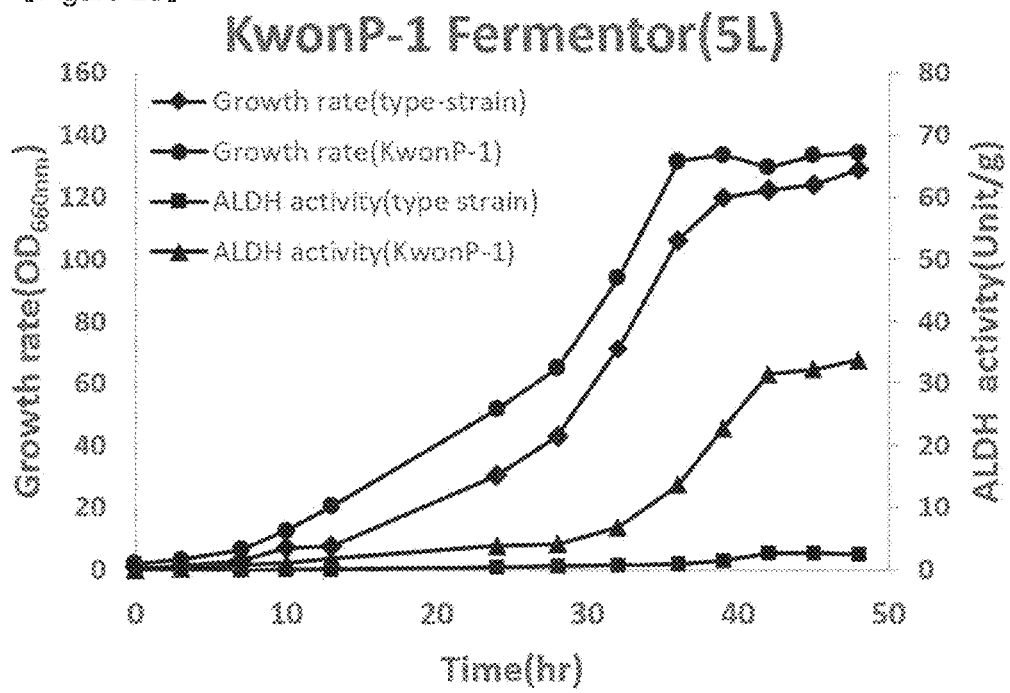
[Figure 24]
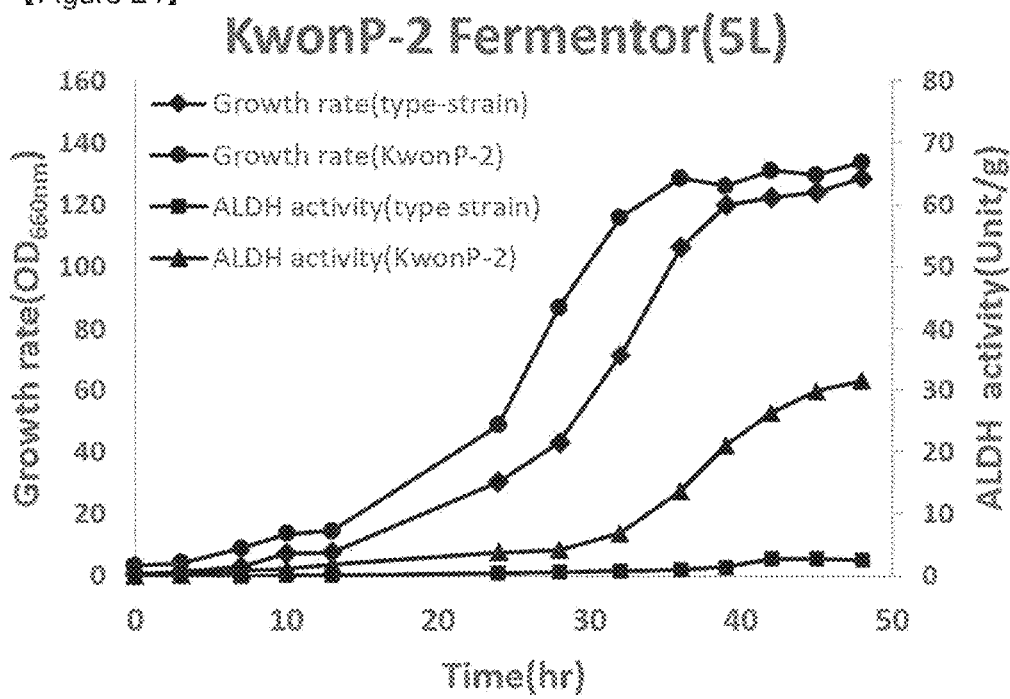

[Figure 25]
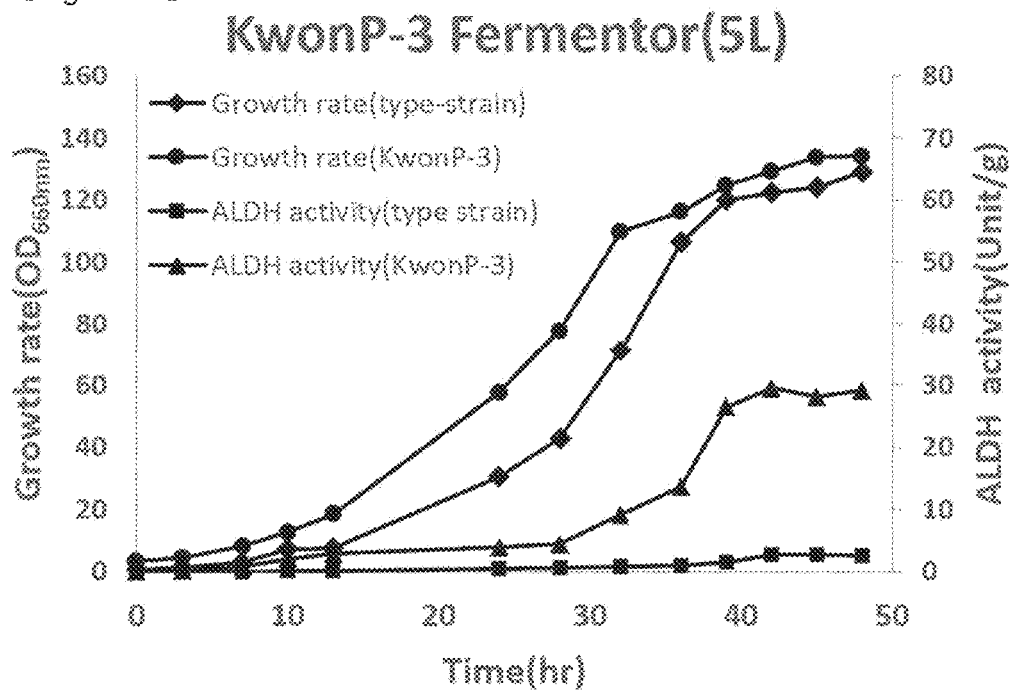
[Figure 26]
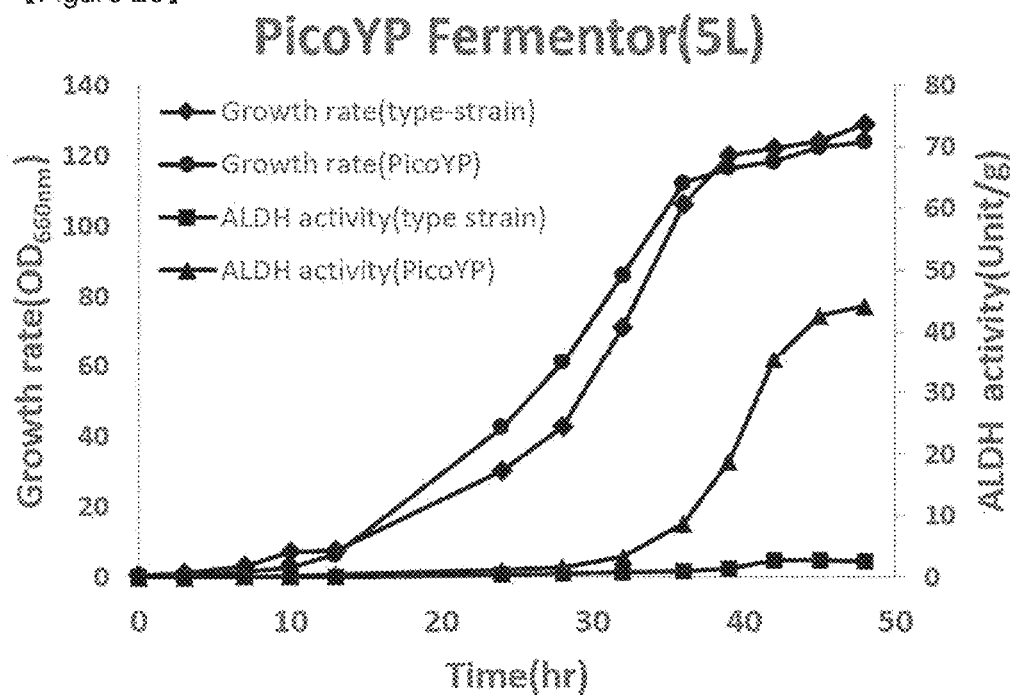

[Figure 27]
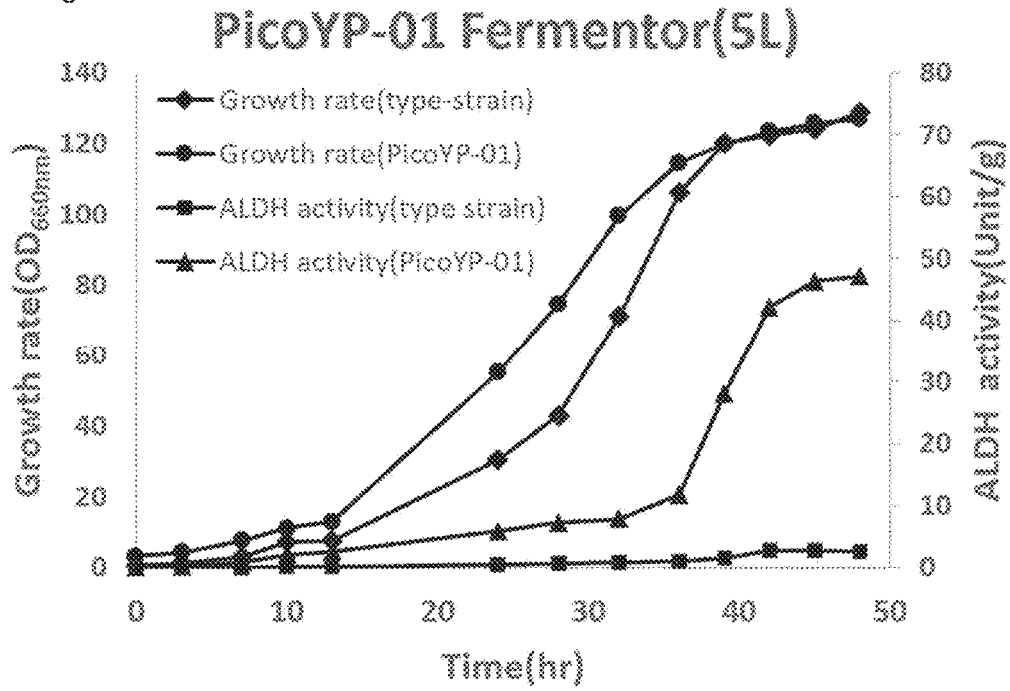
[Figure 28]
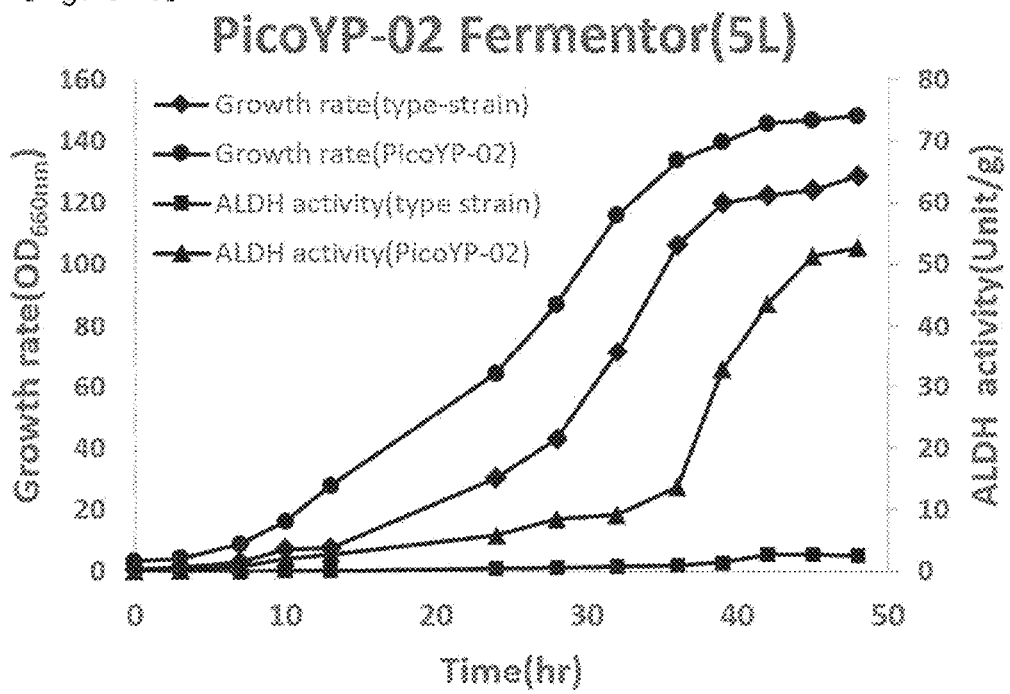

SEQUENCE LISTING

```
Sequence total quantity: 5
SEQ ID NO: 1            moltype = DNA  length = 3054
FEATURE                 Location/Qualifiers
source                  1..3054
                        mol_type = genomic DNA
                        organism = Saccharomyces cerevisiae
SEQUENCE: 1
atgcctacct tgtatactga tatcgaaatc ccacaattga aaatctcttt aaagcaaccg   60
```

```
ctagggttgt ttatcaacaa tgagttttgt ccatcatcag atggaaagac catcgaaact   120
gtgaacccag ctactggcga accgataaca tccttccaag cagctaacga aaaggatgta   180
gacaaagctg tgaaagctgc cagggctgct tttgataacg tttggtcgaa gacatcttct   240
gagcaacgtg gtatttatct ttcaaactta ttaaaactta ttgaggagga gcaagacaca   300
cttgccgcat tagagacttt agacgctgga aagccttacc attcaaatgc caaaggtgat   360
ttggcacaaa ttttacagct taccagatat tttgctgggt ccgctgataa gtttgacaaa   420
ggtgcaacca taccattgac ttttaacaag tttgcatata ctctaaaagt tccttttggc   480
gttgttgctc aaatcgttcc atggaattat cctctagcta tggcttgttg gaaattgcaa   540
ggtgccttag cagccggtaa cacggttatc atcaaacctg ctgagaatac ctctctatct   600
ctactttatt ttgctacttt aattaaaaaa gcaggttttc cacctggtgt tgtcaatatc   660
gttcctggtt atggatcact tgtaggccaa gccctagcat ctcacatgga tatcgacaaa   720
atatctttta cgggaagcac caaggtcggt ggatttgtgt tggaagcttc cggccaatcg   780
aaccttaaag acgttacact agaatgcggt ggtaagtctc ctgctctcgt atttgaagat   840
gcagaccttg ataaggctat cgattggata gcagctggca ttttctacaa ttcaggacag   900
aattgtaccg caaactcaag agtttatgtt caaagttcga tctacgacaa gtttgttgaa   960
aagtttaaag aaactgcaaa gaaggagtgg gatgttgcag gaaaatttga tccgtttgat  1020
gagaaatgca tcgttggtcc agttatatca agtacacagt atgaccgcat caaaagttac  1080
atagaacgtg gtaaaaggga ggaaaagttg gacatgttcc agacctctga atttcctatt  1140
ggtggagcta aaggctactt cattccccca accatcttca ctgatgtccc gcaaacatcg  1200
aaaactgttac aggatgagat atttggcccg gttgtggttg ttagcaagtt cacaaattat  1260
gatgacgctc tgaagctggc taatgatact tgctacgggc tcgcctctgc ggtcttcaca  1320
aaagatgtca agaaagcgca catgtttgct cgcgatatta agcaggaac tgtttggatc  1380
aactcatcta cgatgaaga tgttaccgtt ccttttggcg ggtttaaaat gagtggtatt  1440
ggtagagaac tggggcaaag tggtgttgat acctatcttc aaacaaaagc aagatataga  1500
ttatacacat ttagaaaatt agccaaaaga aaaatgccta ccttgtatac tgatatcgaa  1560
atcccacaat tgaaaatctc tttaaagcaa ccgctagggt tgtttatcaa caatgagttt  1620
tgtccatcat cagatggaaa gaccatcgaa actgtgaacc cagctactgg cgaaccgata  1680
acatccttcc aagcagctaa cgaaaaggat gtagacaaag ctgtgaaagc tgccagggct  1740
gcttttgata acgtttggtc gaagacatct tctgagcaac gtggtattta tctttcaaac  1800
ttattaaaac ttattgagga ggagcaagac acacttgccg cattagagac tttagacgct  1860
ggtaagcctt tccattccaa tgctaaacaa gacttagccc agattataga acttacaaga  1920
tactatgcgg gggcggtcga caagttcaat atgggtgaaa ccattccatt gacttttaac  1980
aagtttgcat atactctaaa agttccttt ggcgttgttg ctcaaatcgt tccatggaat  2040
tatcctctag ctatggcttg tagaaaaatg caaggtgcct tagcggccgg taacacggtt  2100
atcatcaaac ctgctgaaaa tacctctcta tctctacttt attttgctac tttaattaaa  2160
aaagcaggtt ttcccacctgg tgttgtcaat gtcattcctg gttatggttc cgttgtgggg  2220
aaagctttag gaacccacat ggatatcgac aaaatatctt ttacgggaag tactaaggtt  2280
ggcggctcag tattggaagc ttccggccaa tcgaaccttaaggatatcac actagaatgc  2340
ggtggtaagt ctcctgctct tgtatttgaa gatgcagacc ttgataaggc tatagaatgg  2400
gtagcaaatg gtattttttt taattcggga cagatctgca ctgcaaactc aagagtttat  2460
gttcaaagtt cgatctacga caagtttgtt gaaaagttta agaaactgc aaagaaggag  2520
tgggatgttg caggaaaatt tgatccgttt gatgagaaat gcatcgttgg tccagttata  2580
tcaagtacac agtatgaccg catcaaaagt tacatagaac gtggtaaaaa gggaggaaaa  2640
ttggacatgt tccagacctc tgaatttcct attggtggag ctaaaggcta cttcattccc  2700
ccaaccatct tcactgatgt accagaaaca tctaagttgc tgcgtgatga aatatttggc  2760
ccggttgtgg ttgttagcaa gttcacaaat tatgatgacg ctctgaagct ggctaatgat  2820
acttgctacg ggctcgcctc tgcggtcttc accaaagatg tcaagaaagc gcacatgttt  2880
gctcgcgata ttaaagcagg aactgtttgg atcaatcaaa ccaatcaaga agaagctaaa  2940
gttccttttg gcggatttaa gatgagtggt attggtagag aatcaggcga caccggcgtt  3000
gataactatt tacaaataaa atcagtccat gtggatcttt cattggataa ataa        3054

SEQ ID NO: 2           moltype = DNA   length = 42
FEATURE                Location/Qualifiers
source                 1..42
                       mol_type = genomic DNA
                       organism = Saccharomyces cerevisiae
SEQUENCE: 2
agatatagat tatacacatt tagaaaatta gccaaaagaa aa                       42

SEQ ID NO: 3           moltype = DNA   length = 1521
FEATURE                Location/Qualifiers
source                 1..1521
                       mol_type = genomic DNA
                       organism = Saccharomyces cerevisiae
SEQUENCE: 3
atgcctacct tgtatactga tatcgaaatc ccacaattga aatctctttt aaagcaaccg    60
ctagggttgt ttatcaacaa tgagttttgt ccatcatcag atggaaagac catcgaaact   120
gtgaacccag ctactggcga accgataaca tccttccaag cagctaacga aaaggatgta   180
gacaaagctg tgaaagctgc cagggctgct tttgataacg tttggtcgaa gacatcttct   240
gagcaacgtg gtatttatct ttcaaactta ttaaaactta ttgaggagga gcaagacaca   300
cttgccgcat tagagacttt agacgctgga aagccttacc attcaaatgc caaaggtgat   360
ttggcacaaa ttttacagct taccagatat tttgctgggt ccgctgataa gtttgacaaa   420
ggtgcaacca taccattgac ttttaacaag tttgcatata ctctaaaagt tccttttggc   480
gttgttgctc aaatcgttcc atggaattat cctctagcta tggcttgttg gaaattgcaa   540
ggtgccttag cagccggtaa cacggttatc atcaaacctg ctgagaatac ctctctatct   600
ctactttatt ttgctacttt aattaaaaaa gcaggttttc cacctggtgt tgtcaatatc   660
gttcctggtt atggatcact tgtaggccaa gccctagcat ctcacatgga tatcgacaaa   720
atatctttta cgggaagcac caaggtcggt ggatttgtgt tggaagcttc cggccaatcg   780
aaccttaaag acgttacact agaatgcggt ggtaagtctc ctgctctcgt atttgaagat   840
```

```
gcagaccttg ataaggctat cgattggata gcagctggca ttttctacaa ttcaggacag    900
aattgtaccg caaactcaag agtttatgtt caaagttcga tctacgacaa gtttgttgaa    960
aagtttaaag aaactgcaaa gaaggagtgg gatgttgcag gaaaatttga tccgtttgat   1020
gagaaatgca tcgttggtcc agttatatca agtacacagt atgaccgcat caaaagttac   1080
atagaacgtg gtaaaaggga ggaaaagttg gacatgttcc agacctctga atttcctatt   1140
ggtggagcta aaggctactt cattccccca accatcttca ctgatgtccc gcaaacatcg   1200
aaactgttac aggatgagat atttggcccg gttgtggttg ttagcaagtt cacaaattat   1260
gatgacgctc tgaagctggc taatgatact tgctacgggc tcgcctctgc ggtcttcaca   1320
aaagatgtca agaaagcgca catgtttgct cgcgatatta aagcaggaac tgtttggatc   1380
aactcatcta acgatgaaga tgttaccgtt cctttggcg ggtttaaaat gagtggtatt    1440
ggtagagaac tggggcaaag tggtgttgat acctatcttc aaacaaaagc agttcacata   1500
aatctctctt tggacaacta a                                             1521

SEQ ID NO: 4           moltype = DNA  length = 1521
FEATURE                Location/Qualifiers
source                 1..1521
                       mol_type = genomic DNA
                       organism = Saccharomyces cerevisiae
SEQUENCE: 4
atgcctacct tgtatactga tatcgaaatc ccacaattga aaatctcttt aaagcaaccg     60
ctagggttgt ttatcaacaa tgagttttgt ccatcatcag atggaaagac catcgaaact    120
gtgaacccag ctactggcga accgataaca tccttccaag cagctaacga aaaggatgta    180
gacaaagctg tgaaagctgc cagggctgct tttgataacg tttggtcgaa gacatcttct    240
gagcaacgtg gtatttatct ttcaaactta ttaaaactta ttgaggagga gcaagacaca    300
cttgccgcat tagagacttt agacgctggt aagcctttcc attccaatgc taaacaagac    360
ttagcccaga ttatagaact tacaagatac tatgcgggg cggtcgacaa gttcaatatg     420
ggtgaaacca ttccattgac ttttaacaag tttgcatata ctctaaaagt tcctttggc    480
gttgttgctc aaatcgttcc atggaattat cctctagcta tggcttgtag aaaaatgcaa    540
ggtgccttag cggccggtaa cacggttatc atcaaacctg ctgaaaatac ctctctatct    600
ctactttatt ttgctacttt aattaaaaaa gcaggttttc cacctggtgt tgtcaatgtc    660
attcctggtt atggttccgt tgtgggaaa gctttaggaa cccacatgga tatcgacaaa     720
atatctttta cgggaagtac taaggttggc ggctcagtat tggaagcttc cggccaatcg    780
aaccttaagg atatcacact agaatgcggt ggtaagtctc ctgctcttgt atttgaagat    840
gcagaccttg ataaggctat agaatgggta gcaaatggta tttttttaa ttcgggacag     900
atctgcactg caaactcaag agtttatgtt caaagttcga tctacgacaa gtttgttgaa    960
aagtttaaag aaactgcaaa gaaggagtgg gatgttgcag gaaaatttga tccgtttgat   1020
gagaaatgca tcgttggtcc agttatatca agtacacagt atgaccgcat caaaagttac   1080
atagaacgtg gtaaaaagga ggaaaagttg gacatgttcc agacctctga atttcctatt   1140
ggtggagcta aaggctactt cattccccca accatctca ctgatgtacc agaaacatct    1200
aagttgctgc gtgatgaaat atttggcccg gttgtggttg ttagcaagtt cacaaattat   1260
gatgacgctc tgaagctggc taatgatact tgctacgggc tcgcctctgc ggtcttcacc   1320
aaagatgtca agaaagcgca catgtttgct cgcgatatta aagcaggaac tgtttggatc   1380
aatcaaacca atcaagaaga agctaaagtt cctttggcg gatttaagat gagtggtatt    1440
ggtagagaat caggcgacac cggcgttgat aactatttac aaataaaatc agtccatgtg   1500
gatctttcat tggataaata a                                             1521

SEQ ID NO: 5           moltype = DNA  length = 829
FEATURE                Location/Qualifiers
source                 1..829
                       mol_type = genomic DNA
                       organism = Saccharomyces cerevisiae
SEQUENCE: 5
ggatcttttcc gtagggtgaa cctggcggag agggatcatt aaagaaattt aataattttg     60
aaaatggatt tttttgtttt ggcaagagca tgagagcttt tactgggcaa gaagacaaga    120
gatggagagt ccagccgggc ctgcgcttaa gtgcgcggtc ttgctaggct tgtaagtttc    180
tttcttgcta ttccaaacgg tgagagattt ctgtgcttt gttataggac aattaaaacc     240
gtttcaatac aacacactgt ggagttttca tatctttgca acttttctt tgggcattcg     300
agcaatcggg gcccagaggt aacaaacaca acaattttta tctattcatt aaattttgt     360
caaaaacaag aattttcgta actggaaatt ttaaaatatt aaaaactttc aacaacggat    420
ctcttggttc tcgcatcgat gaagaacgca gcgaaatgcg atacgtaatg tgaattgcag    480
aattccgtga atcatcgaat cttgtgaacgc acattgcgcc ccttggtatt ccaggggca    540
tgcctgtttg agcgtcattt ccttctcaaa cattctgttt ggtagtgagt gatactcttt    600
ggagttaact tgaaattgct ggccttttca ttggatgttt tttccaaa gagaggtttc     660
tctgcgtgct tgaggtataa tgcaagtacg gtcgttttga gttttaccaa ctgcggctaa    720
tctttttta tactgagcgt attggaacgt tatcgataag aagagagcgt ctaggcgaac    780
aatgttctta aagtttgacc tcaaatccag gtaggagtcc ccaacgccc                829
```

FOOD COMPOSITION CONTAINING NOVEL ALDEHYDE DEHYDROGENASE FOR IMPROVING MEMORY AND COGNITIVE FUNCTION

CROSS-REFERENCE TO RELATED APPLICATION

The present application is a continuation of U.S. patent application Ser. No. 18/519,546, filed on Nov. 27, 2023, which is based upon and claims the benefit of priority from Korean Patent Application No. 10-2022-0165816, filed Dec. 1, 2022, and Korean Patent Application No. 10-2023-0153059, filed Nov. 7, 2023, the entire contents of each of which are incorporated herein by reference.

REFERENCE TO A SEQUENCE LISTING

In accordance with 37 CFR § 1.831, the present specification makes reference to a Sequence Listing submitted electronically as an .xml file named "PKPA2204KRPRIUSA1.xml". The .xml file was generated on Jan. 12, 2024, and is 13000 bytes in size. The entire contents of the Sequence Listing are hereby incorporated by reference.

TECHNICAL FIELD

The present invention relates to food and pharmaceutical compositions for improving memory and cognitive function containing a novel aldehyde dehydrogenase (ALDH). The compositions of the present invention reduce the abnormal aggregation of pathogenic or lesional proteins in the brain by reducing oxidative stress and reducing inflammation in brain tissue. That is, the present invention is directed to a food composition or a pharmaceutical composition that inhibit or prevent various neuro-degenerative diseases caused by accumulation of lesional proteins in brain tissue.

More specifically, the compositions of the present invention contain a novel aldehyde dehydrogenase derived from a novel mutant yeast, that improve memory and cognitive function. The present invention relates to a food and pharmaceutical composition for preventing Alzheimer's disease and Huntington disease by reducing the accumulation of lesional proteins in brain tissue.

The composition of the present invention contains aldehyde dehydrogenase (ALDH), coenzymes (NAD, NADP), glutathione, etc., thereby inhibit Alzheimer's dementia. More specifically the food or pharmaceutical compositions of the present invention contain a lysate of any one or a mixture thereof selected from the group consisting of *Saccharomyces cerevisiae*, KCTC13925BP, KCTC14122BP, KCTC14123BP, KCTC14983BP, KCTC14984BP and KCTC14985BP.

BACKGROUND

Dementia refers to a clinical syndrome in which cognitive functions such as memory, language, and judgment are weakened, making normal life impossible. Representative examples of dementia include Alzheimer's disease, vascular dementia, Lewy body dementia, and frontotemporal dementia.

According to histopathological studies, dementia is known to begin with damage to neurons in the hippocampus, a specific part of the brain responsible for memory and cognition, and to spread throughout the brain. Dementia is a late-onset disease symptom caused by various causes, such as environmental factors such as drinking, smoking, and taking medicines, and the effects of various diseases. It is known that any disease or lifestyle that can cause damage to brain function can be a cause of dementia.

Excessive alcohol consumption generates excessive amounts of acetaldehyde in the human body, causing oxidative stress in brain tissue. It has been reported that oxidative stress in brain tissue causes neuroinflammation, generates abnormal aggregates of amyloid protein, and causes dementia.

In addition to the above amyloid protein aggregates, it has been known that synaptic dysfunction caused by hyperphosphorylation of tau protein, which plays an important role in maintaining the shape of brain cell tissue, causes dementia. In addition, it has also been known that increased brain nerve inflammation, increased oxidative stress, dysfunction of mitochondria and synapses, and inhibition of neurotransmitter metabolism damage brain cells and cause dementia.

Senile plaques, a representative brain pathology, are associated with the aggregation of beta-amyloid protein, and fascicles of nerve fibers are associated with tau protein hyperphosphorylation.

In addition, it is known that abnormal accumulation of alpha-synuclein ($\alpha$-Syn) protein aggregates in neurons, nerve fibers, or glial cells causes neurodegenerative diseases.

As a result, modified proteins such as beta-amyloid protein, hyperphosphorylated tau protein, or abnormal aggregates of alpha-synuclein accumulate abnormally in neurons or glial cells, inducing inflammation in nerves or increasing oxidative stress, causing dementia. These modified proteins act as a toxin on nerve cells and consequently, cause degenerative nerve diseases.

Amyloid protein is formed by polymerizing several monomeric peptides to form a fibrous shape. Amyloid and amyloid plaques, which are abnormal aggregates of these fiber-forming proteins, are generally toxic to nerve cells.

Amyloid plaques are toxic to cells by reducing the function of cellular calcium ion channels and intracellular mitochondria and increasing the concentration of reactive oxygen species (ROS) within cells.

Amyloid plaques reduce the function of cellular calcium ion channels and intracellular mitochondria and increase the concentration of reactive oxygen species (ROS) within cells, leading to brain cell death.

Tau protein is mainly present in the axon region of nerve cells, and plays a role in stabilizing the structure of nerve cells by attaching to the intracellular skeleton (microtubules).

However, when tau protein is separated from the intracellular skeleton, environmental factors cause aggregation of tau protein, leading to the death of nerve cells. As a result, when amyloid beta and tau proteins accumulate in brain tissue, they damage synapses, which are memory storage locations in the brain, or connections where communication between nerve cells occurs. It has been known that such damage causes cognitive disorders such as memory loss.

Lewy body dementia is characterized by the occurrence of Lewy bodies and Lewy neuritis in cells containing high concentrations of aggregated alpha-synuclein.

In the early stages of Alzheimer's symptoms, alpha-synuclein is a pathogenic substance. As amyloid plaques and tau protein aggregate, Alzheimer's symptoms become more severe.

A drug that completely treats dementia has not yet been developed, and research and development on various drugs to treat dementia is currently in progress. Current dementia treatments are drugs that aim to relieve symptoms caused by dementia or prevent dementia symptoms from worsening.

Acetylcholinesterase inhibitor (ACE Inhibitor) drugs such as donepezil, rivastigmine, galantamine, and NMDA receptor antagonist (N-methyl-D-aspartate receptor antagonist) drugs such as Memantine, are used for treatment of dementia.

These drugs for treating dementia improve the symptoms of dementia patients by inhibiting the action of enzymes that decompose acetylcholine in brain tissue, thereby increasing the amount of acetylcholine in brain tissue.

However, the therapeutic effectiveness of these drugs for advanced dementia is reduced, and they cause side effects such as nausea, diarrhea, loss of appetite, muscle cramps, and sleep disorders.

Recently, many clinical trials to verify the effectiveness of dementia treatments aimed at blocking protein aggregation have failed. Therefore, research to determine the exact cause of dementia and new treatment strategies for dementia are being discussed.

The present inventor has prepared a composition containing a new aldehyde dehydrogenase enzyme that reduces oxidative stress in brain nerve cells, alleviates inflammation in nerve tissue, and reduces amyloid plaque accumulation in brain tissue. The composition of the present invention can be used as a food composition and pharmaceutical composition for suppressing Alzheimer's disease by reducing the apoptosis of brain cells.

SUMMARY

Therefore, the basic purpose of the present invention is to provide a food composition that improves memory and cognitive function, and a pharmaceutical composition that suppress the accumulation of abnormal amyloid protein in brain nerve tissue, which contain a novel aldehyde dehydrogenase that promotes the acid conversion of endogenous aldehydes generated by in vivo decomposition of alcohol or oxidation of endogenous amine compounds such as dopamine, norepinephrine, serotonin, and gamma-aminobutyric acid (GABA).

Another object of the present invention is to provide a food composition that improves memory and cognitive function and a pharmaceutical composition for the treatment of Alzheimer's Dementia, containing any one or a mixture thereof (hereinafter, abbreviated as KARC) selected from the group consisting of *Saccharomyces cerevisiae* KCTC13925BP, KCTC14122BP, KCTC14123BP, KCTC14983BP, KCTC14984BP, and KCTC14985BP.

The primary object of the present invention as described above can be accomplished by providing a composition which contains novel aldehyde dehydrogenase that promotes the acid conversion of endogenous aldehydes generated by the decomposition of endogenous alcohol or the oxidation of endogenous amine compounds such as dopamine, norepinephrine, serotonin, and gamma aminobutyric acid (GABA).

Another object of the present invention can also be achieved by providing a food composition that improves memory and cognitive function and a pharmaceutical composition for the treatment of Alzheimer's Dementia, containing any one or a mixture thereof selected from the group consisting of *Saccharomyces cerevisiae* KCTC13925BP, KCTC14122BP, KCTC14123BP, KCTC14983BP, KCTC14984BP, and KCTC14985BP.

In the brain of Alzheimer's mice administered orally with the dried powder or lysate of any one or a mixture thereof selected from the group consisting of *Saccharomyces cerevisiae* KCTC13925BP, KCTC14122BP, KCTC14123BP, KCTC14983BP, KCTC14984BP, and KCTC14985BP of the present invention, the oxidative stress was reduced, astrocytes and microglia activated by inflammatory reactions were decreased, and amyloid aggregation and plaques were reduced. In addition to these effects, the pharmaceutical effect of recovering memory and cognitive abilities were verified.

BRIEF DESCRIPTION OF DRAWINGS

FIG. 1 is a graph showing the ability of KARC to decompose acetaldehyde in vivo.

FIG. 2 is a graph showing the ability of KARC to decompose malondialdehyde in vivo.

In animal experiments in which blood acetaldehyde FIG. 1 and blood malondialdehyde FIG. 2 which are endogenous toxic aldehydes, were increased by consuming alcohol, the aldehyde reduction and oxidative stress reduction effects of KARC were confirmed.

FIG. 3 is a graph showing the ability of KARC to decompose acetaldehyde in the human body.

FIG. 4 is a graph showing the ability of KARC to decompose malondialdehyde in the human body.

FIG. 5 is a graph showing stabilization of malondialdehyde in the human body by KARC.

In a test for confirming the reduction of endogenous blood acetaldehyde in the human body FIG. 3 and blood malondialdehyde reduction FIG. 4, the effect of administration of KARC appear to reduce acetaldehyde and malondialdehyde, which are biomarkers of hangover, fatigue, and cardiovascular disease.

FIG. 5 shows the effect of lowering oxidative stress by lowering malondialdehyde, a biomarker of oxidative stress and active oxygen, by administration of KARC in a state where oxidative stress was increased due to taking medicine, etc.

FIG. 6 shows the schedule and drug content for producing an Alzheimer's model by using 5×FAD mice.

FIG. 7 shows the results of the Y-maze test of the Alzheimer's model by KARC.

In a maze experiment evaluating short-term memory after inducing Alzheimer's disease using 5×FAD mice, the number of times visiting a new maze decreased to 47.4%, showing a decrease in cognitive ability.

However, in the mouse group administered KARC, it is observed that cognitive ability was recovered by increasing to 65.02%. This shows that KARC can improve memory impairment caused by Alzheimer's and can be a treatment for preventing cognitive decline caused by degenerative brain diseases and improving reduced cognitive function.

FIG. 8 shows the effect of reducing amyloid plaques in the entire brain of an Alzheimer's model by KARC.

FIG. 9 shows the result of intensity reduction of amyloid plaques in the hippocampus region of the Alzheimer's model by KARC.

FIG. 10 shows the results of reduction in the number of amyloid plaques in the hippocampus of an Alzheimer's model by KARC.

After Alzheimer's induction by using 5×FAD mice, amyloid plaques deposited in brain tissue abnormally increased, but reduced by KARC FIG. 8, actual amyloid plaque size decreased FIG. 9, and number also decreased FIG. 10. Therefore, the effectiveness of KARC for preventing and treating neurodegenerative diseases such as dementia by reducing a modified protein and amyloid plaques, appears.

FIG. 11 shows the results of immunostaining for the increase in inflammatory response due to activation of microglia in the hippocampus of an Alzheimer's model mouse.

FIG. 12 shows the results of measuring the number of activated microglia in the CA1 region of the hippocampus of an Alzheimer's model mouse by administration of KARC.

FIG. 13 shows the results of measuring the number of activated microglia in the CA3 region of the hippocampus of an Alzheimer's model mouse by administration of KARC.

In Alzheimer's mice, the degree of microglial activation, which indicates the degree of inflammation of microglia, known to be the cause of brain neuron death, appears through immunostaining for Iba-1. In the KARC administration group, the degree of activated microglia decreased FIG. 11, and the number of activated microglia in the CA1 and CA3 regions of the hippocampus, which stores memories, also decreased FIGS. 12 and 13. Therefore, the prevention and treatment effects of cranial nerve inflammatory response by KARC administration in Alzheimer's model animals appears.

FIG. 14 shows the results of immunostaining for changes in inflamed astrocytes in the hippocampus of an Alzheimer's model mouse by administration of KARC.

FIG. 15 shows the results of measuring the number of activated astrocytes in the CA1 region of the hippocampus of an Alzheimer's model mouse by administration of KARC.

FIG. 16 shows the results of measuring the number of activated astrocytes in the CA3 region of the hippocampus of an Alzheimer's model mouse by administration of KARC.

In Alzheimer's mice, inflammation of astrocytes causes the death of brain neurons and simultaneously leads to a weakening of brain homeostasis through the creation and maintenance of cranial nerve synapses.

As a result of confirming the degree of astrocyte activation through immunostaining for GFAP, which is a measure of the inflammatory response of astrocytes, the degree of astrocyte activation decreases in the KARC administration group FIG. 14, and the level of activation of the hippocampus which stores memories, decreases. The number of astrocytes in the CA1 and CA3 areas decreases FIGS. 15, 16, and the inflammation reduction effect appears in the KARC administered group.

FIG. 17 shows changes in enzyme activity in case of oral administration of KwonP-1 strain.

FIG. 18 shows changes in enzyme activity in case of oral administration of KwonP-2 strain.

FIG. 19 shows changes in enzyme activity in case of oral administration of KwonP-3 strain.

FIG. 20 shows changes in enzyme activity in case of oral administration of Pico YP strain.

FIG. 21 shows changes in enzyme activity in case of oral administration of Pico YP-01 strain.

FIG. 22 shows changes in enzyme activity in case of oral administration of Pico YP-02 strain.

FIGS. 17, 18, 19, 20, 21, 22 shows KwonP-1, KwonP-2, KwonP-3, PicoYP, Pico YP-01, and Pico YP-02 were orally administered under conditions (1<pH<5) similar to the digestive process of the stomach in human for 90 minutes. The change in ALDH enzyme activity were measured. ALDH enzyme activity was maintained at a minimum of 37.29 unit/g and a maximum of 52.24% at pH=5 (similar to condition observed during food intake). It was confirmed that the enzyme activity was maintained when KARC was administered orally.

FIG. 23 shows the growth curve and enzyme activity of KwonP-1 strain cultured in a 5 L fermenter.

FIG. 24 shows the growth curve and enzyme activity of KwonP-2 strain cultured in a 5 L fermenter.

FIG. 25 shows the growth curve and enzyme activity of KwonP-3 strain cultured in a 5 L fermenter.

FIG. 26 shows the growth curve and enzyme activity of Pico YP strain cultured in a 5 L fermenter.

FIG. 27 shows the growth curve and enzyme activity of PicoYP-01 strain cultured in a 5 L fermenter.

FIG. 28 shows the growth curve and enzyme activity of PicoYP-02 strain cultured in a 5 L fermenter.

In FIGS. 23, 24, 25, 26, 27, 28, the novel mutant strains: KwonP-1, KwonP-2, KwonP-3, PicoYP, PicoYP-01, and Pico YP-01 were respectively cultured using YPD medium in a 5 L fermenter under the same conditions. It was carried out at 30° C. and 200 rpm for 48 hours. When comparing the growth curve (OD660 nm) and ALDH enzyme activity of each strain with that of the type strain, ALDH enzyme activity was at least 10.5 times and up to 18.75 times higher. PicoYP-01 had the highest ALDH activity at 52.68 unit/g, and KwonP-3 had the lowest at 29.5 unit/g.

BEST MODEL

Hereinafter, the method for producing dry powder of KARC of the present invention, the lysate of *Saccharomyces cerevisiae* KCTC13925BP, KCTC14122BP, KCTC14123BP KCTC14983BP, KCTC14984BP, KCTC14985BP, will be described in more detail.

However, these examples are for illustrative purposes only of compositions that can achieve the purpose of the present invention, and therefore, the scope of the present invention is not limited only to the compositions described in the following examples.

DETAILED DESCRIPTION OF THE EMBODIMENTS

[Example 1] Screening Wild Yeast Parent Strain to Proceed Mutation

In the present invention, each suspension of traditional Korean wines (hereinafter referred to as makgeolli) was prepared by mixing various types of makgeolli with a 0.9% NaCl solution. The makgeolli suspension was stirred at 200 rpm for 1 hour. The supernatant containing the yeast wild strain was diluted with YPD yeast extract peptone dextrose broth) medium. The diluted solution was prepared to be 106 times the original solution.

The diluted solution was smeared on YPD agar medium. The agar medium was statically cultured at 30° C. under aerobic conditions for one week. *Saccharomyces cerevisiae* was primary screened based on morphological characteristics of colonies, growth characteristics at YM medium and microscopic observation.

The ALDH activity and glutathione content of screened *Saccharomyces cerevisiae* were measured. Parent strain was selected based on ALDH activity and glutathione production.

1-1: Measurement of Aldehyde Dehydrogenase

Acetaldehyde reacted with Dinitrophenylhydrazine (DNPH) to form acetaldehyde-hydrazone (Ach-DNPH) compound. Ach-DNPH compounds were detected at 360 nm by HPLC equipped with a C18 column. The amount of aldehyde reduced by the decomposition reaction by aldehyde dehydrogenase ALDH) was quantified through the amount of the detected Ach-DNPH compound.

The enzyme reaction was carried out at 30° C. by adding 10 ul of the yeast lysate to 990 ul reaction mixture [50 mM potassium phosphate buffer (pH 8.0), 1.5 mM acetaldehyde and 3 mM NADP+]. After the enzyme reaction was completed, 50 ul of 10 mM DNPH was added to induce the formation of Ach-DNPH. Ach-DNPH formation proceeded at 22° C. for 1 hour.

Ach-DNPH formation was terminated by addition of 3M sodium acetate (pH 9). The Ach-DNPH compound formed was separated by adding twice volume of acetonitrile. The separated Ach-DNPH compound (in ACN) was analyzed by injection into HPLC.

The concentration of the Ach-DNPH compound was analyzed at a wavelength of 360 nm by setting HPLC under the condition of developing a mobile phase (acetonitrile, water) on a C18 column at a rate of 1 ml/min. The area value of the chromatogram obtained as a result of HPLC was converted using the material standard curve of aldehyde-DNPH (Sigma-Aldrich) to quantify the concentration of the Ach-DNPH compound. The reduced concentration of Ach-DNPH per minute, 1 mM, was calculated as 1 unit of ALDH. The activity of ALDH was standardized as Unit/mg-protein.

1-2: Glutathione Measurement

Yeast cells were harvested by centrifuging 1 ml of Saccharomyces cerevisiae culture medium. A suspension was prepared by adding 1 ml of water to the harvested yeast cells. Glutathione was extracted by stirring the suspension at 1,000 rpm at 85° C. for 2 hours. The suspension was centrifuged to remove yeast cells, and the supernatant was filtered through a 0.22 μm filter to obtain a sample containing glutathione.

The concentration of glutathione in the sample was analyzed by HPLC (Shimazu LC-20AD) equipped with a C18 column. The concentration of glutathione was analyzed at a wavelength of 210 nm under conditions in which the mobile phase (2.02 g/L Sodium 1-heptanesulfonate monohydrate, 6.8 g/L Potassium dihydrogen phosphate, pH 3.0, methanol mixture) was developed at a rate of 1 ml/min. The area value of the chromatogram obtained as a result of HPLC was analyzed using the standard curve of glutathione.

ALDH activity and glutathione content were analyzed for 200 different types of yeast obtained from Korean makgeolli. The 10 types of yeast listed in [Table 1] had higher ALDH activity or glutathione production ability than other yeasts.

The ALDH activity of Yeast #97 was 0.10 Unit/mg-protein, the second highest overall. The glutathione content of Yeast #97 was 0.42%, the highest among all yeast #97 was selected as the parent strain and a mutation induction procedure was performed.

TABLE 1

| strain | ALDH activity (Unit/mg-protein) | Glutathione content (%) | Screening |
|---|---|---|---|
| Yeast #6 | 0.06 | 0.38 | |
| Yeast #18 | 0.11 | 0.14 | |
| Yeast #22 | 0.08 | 0.38 | |
| Yeast #41 | 0.14 | 0.22 | |
| Yeast #97 | 0.10 | 0.42 | Selected parent strain (Wild-Type) |
| Yeast #109 | 0.10 | 0.36 | |
| Yeast #112 | 0.09 | 0.40 | |
| Yeast #126 | 0.10 | 0.28 | |
| Yeast #168 | 0.11 | 0.38 | |
| Yeast #197 | 0.08 | 0.41 | |

[Example 2] Identification of the Parent Strain Used in the Mutagenesis Process

Identification was performed to confirm the exact species of the wild-type parent strain (Yeast #97, Wild-type yeast). To ensure sufficient yeast cells for DNA extraction, only colonies of a single yeast were plated on YPD agar medium. DNA was extracted using a Genomic DNA prep kit (Hi-Gene™, BIOFACT Co., Ltd., Daejeon, Korea) according to the manufacturer's instructions.

To amplify rRNA gene on ITS region of the yeast, polymerase chain reaction (PCR) was performed on yeast chromosomal DNA using the ITS5 (forward) and ITS4 (reverse) primers. DNA sequencing of PCR result was analyzed.

The DNA sequence of the parent strain was isolated using the Bioedit program. The reverse strand of the PCR result was converted into a paired base sequence through a reverse completion process.

It was confirmed that the sequence of the forward strand matched the paired sequence of the reverse strand by the Cluster X program. The parent strain which was matching the sequence information confirmed through the above experimental process was identified by using the BLAST database provided by the U.S. National Center for Biotechnology Information (NCBI). As a result of identification, it was found that rRNA in the ITS of the parent strain was 100% identical to that of Saccharomyces cerevisiae.

[Example 3] Selection of Mutant Strains With Improved Aldehyde Dehydrogenase Production The mutation induction process for the wild-type Saccharomyces cerevisiae parent strain was conducted according to the method described in U.S. patent application Ser. No. 17/176,365.

To induce mutations in the yeast parent strain, wild yeast strains that produce both ALDH and glutathione were treated with ethyl methane sulfonate (EMS) or nitrosoguanidine NGD). Yeast strains in which mutations were induced were exposed to various concentrations of methylglyoxal. A mutant strain with excellent adaptability to methylglyoxal was selected. Selected yeast strains were exposed to various concentrations of lysine. A mutant strain with excellent adaptability to lysine was selected. Thirty mutant strains with excellent adaptability to methylglyoxal and lysine were obtained. Each of the 30 yeasts was evaluated through five characteristics: growth curve, ALDH activity, ADH activity, coenzyme content, and glutathione content.

3-1: Growth Characteristics

Saccharomyces cerevisiae is a crab tree positive microorganism and produces ethanol simultaneously with growth under aerobic conditions. Cultivating yeast with high yields requires Saccharomyces cerevisiae with high ethanol tolerance.

YPD media with different ethanol concentrations (no ethanol, 5%, 7%, and 10%) were prepared. Culture medium of Saccharomyces cerevisiae (yeast) adjusted to OD=1 at 660 nm was prepared. Each mixture of the prepared YPD medium and yeast culture medium was diluted at a ratio of 99:1. Finally, YPD media containing yeast with four different concentrations of alcohol were prepared. Each YPD medium mixed with yeast was cultured with shaking at 30° C. and 200 rpm. The growth curve of the mutant strain was measured every 3 hours for 48 hours. The growth curve of each mutant strains was evaluated through three characteristics: time (or period) of lag phase, specific growth rate OD660 nm/hr) of exponential phase, and maximum density OD660 nm).

The higher concentration of ethanol in YPD medium, the longer the time taken for the lag phase. The maximum density and specific growth rate decreased. As a result of comparing the maximum density of mutant strains at low concentration (ethanol 5%) and high concentration (ethanol 10%), it was found that in the case of nine mutant strains, 50% of growth was even maintained at high concentration compared to growth at low concentration. The growth characteristics of the nine mutant strains that distinguished them from other strains were a short lag phase and a high specific growth rate.

TABLE 2

| # | 5% ethanol | | | 7% ethanol | | | 10% ethanol | | | |
|---|---|---|---|---|---|---|---|---|---|---|
| # | hr | $OD_{660\,nm}$/hr | $OD_{660\,nm}$ | hr | $OD_{660\,nm}$/hr | $OD_{660\,nm}$ | hr | $OD_{660\,nm}$/hr | $OD_{660\,nm}$ | Selection |
| 1 | 9 | 0.6477 | 22.2 | 15 | 0.5210 | 16.5 | 24 | 0.1968 | 4.81 | |
| 2 | 12 | 0.3675 | 12.34 | 24 | 0.1835 | 4.11 | 36 | 0.0140 | 0.212 | |
| 3 | 9 | 0.4285 | 15.8 | 15 | 0.2888 | 9.12 | 24 | 0.0880 | 2.16 | |
| 4 | 15 | 0.9683 | 25.3 | 15 | 0.8815 | 25.3 | 15 | 0.4085 | 12.4 | K-1 |
| 5 | 12 | 0.7368 | 14.12 | 15 | 0.7337 | 12.23 | 21 | 0.2205 | 5.68 | |
| 6 | 12 | 0.2590 | 9 | 15 | 0.1773 | 5.44 | 33 | 0.0353 | 0.448 | |
| 7 | 24 | 0.9664 | 22.3 | 27 | 0.8467 | 16.8 | 30 | 0.2673 | 5.17 | |
| 8 | 6 | 0.7268 | 23 | 9 | 0.6222 | 21.5 | 15 | 0.3778 | 12.11 | K-2 |
| 9 | 6 | 0.8433 | 22.12 | 9 | 0.7484 | 25.34 | 15 | 0.3005 | 9.41 | |
| 10 | 3 | 0.4880 | 14.5 | 18 | 0.2013 | 6.12 | 24 | 0.0808 | 2.14 | |
| 11 | 3 | 0.2766 | 11.15 | 9 | 0.2223 | 8.22 | 24 | 0.0988 | 2.41 | |
| 12 | 6 | 0.7149 | 21.68 | 9 | 0.5969 | 20.52 | 12 | 0.3317 | 11.4 | K-3 |
| 13 | 9 | 0.6106 | 22.4 | 12 | 0.4906 | 16.4 | 15 | 0.1813 | 5.68 | |
| 14 | 12 | 0.6136 | 20.6 | 24 | 0.3060 | 6.85 | 36 | 0.0278 | 0.41 | |
| 15 | 12 | 0.4759 | 15.45 | 18 | 0.1751 | 5.41 | 33 | 0.0707 | 0.896 | |
| 16 | 9 | 0.8533 | 23.8 | 15 | 0.8065 | 20.9 | 21 | 0.4953 | 12.1 | K-4 |
| 17 | 21 | 0.6016 | 14.85 | 24 | 0.3955 | 8.45 | 24 | 0.0547 | 1.26 | |
| 18 | 12 | 0.7766 | 19.25 | 18 | 0.4437 | 12.4 | 24 | 0.1219 | 2.85 | |
| 19 | 3 | 0.5050 | 14.75 | 9 | 0.4463 | 14.6 | 21 | 0.2521 | 6.23 | |
| 20 | 27 | 0.0666 | 1.41 | 36 | 0.0278 | 0.36 | — | — | — | |
| 21 | 3 | 0.6044 | 22.14 | 9 | 0.6051 | 20.64 | 12 | 0.3247 | 11.1 | K-5 |
| 22 | 24 | 0.5798 | 13.4 | 27 | 0.5080 | 10.1 | 30 | 0.1604 | 3.1 | |
| 23 | 15 | 0.6455 | 16.9 | 15 | 0.5877 | 16.9 | 15 | 0.2003 | 6.3 | |
| 24 | 3 | 0.7269 | 20.4 | 6 | 0.6375 | 18.6 | 12 | 0.3522 | 10.5 | K-6 |
| 25 | 9 | 0.4858 | 16.7 | 15 | 0.3908 | 12.4 | 24 | 0.1476 | 3.6 | |
| 26 | 6 | 0.6559 | 17.2 | 9 | 0.5821 | 19.7 | 15 | 0.3177 | 9.6 | K-7 |
| 27 | 9 | 0.2857 | 10.5 | 15 | 0.1925 | 6.1 | 24 | 0.0587 | 1.4 | |
| 28 | 12 | 0.6315 | 12.1 | 15 | 0.6289 | 10.5 | 21 | 0.1890 | 4.9 | |
| 29 | 6 | 0.5451 | 17.3 | 9 | 0.4667 | 16.1 | 15 | 0.2834 | 9.1 | K-8 |
| 30 | 9 | 0.7826 | 21.8 | 9 | 0.6614 | 19.9 | 15 | 0.3267 | 10.6 | K-9 |

3-2: Activity of Alcohol Dehydrogenase (ADH) and Aldehyde Dehydrogenase (ALDH)

The activity of alcohol dehydrogenase (ADH) was measured by adding 10 μl of yeast lysate to 990 μl of the reaction mixture with the composition of 50 mM potassium phosphate buffer (pH 8.0), 2 mM NAD+ and 1% ethanol. The activity of aldehyde dehydrogenase (ALDH) was measured by adding 10 μl of yeast lysate to 990 μl of the reaction mixture with the composition of 50 mM potassium phosphate buffer (pH 8.0), 3 mM NAD+ and 1.5 mM acetaldehyde. The enzymatic reaction of ADH and ALDH was carried out at 30° C. for 5 minutes, and the concentration of NAD(P)H produced as a result of the enzyme reaction was measured through absorbance at 340 nm.

The enzyme activities of nine mutant strains (K-1 to K-9) selected in the present invention were measured. The ADH activity of the mutant strain was a minimum of 382.69 units/g and a maximum of 975.29 units/g. The ADH activity of the mutant strain increased at least 5.1 times and up to 13.1 times compared to the type strain (reference yeast, Saccharomyces cerevisiae KCTC7296). The ALDH activity of the mutant strain was a minimum of 15.23 unit/g and a maximum of 72.16 unit/g. The ALDH activity of the mutant strain increased by at least 5.3 and up to 24.9 times compared to the enzyme activity of the type-strain.

Six mutant strains (K-1, 4, 6, 7, 8, and 9) showed similar increase rate of enzyme activity of ADH and ALDH compared to the type strain. The enzyme activity of ALDH in the three mutant strains (K-2, 3, and 5) was 18.3, 23.2 and 24.9 times higher, respectively, compared to the type-strain. The enzyme activity of ADH in the three mutant strains (K-2, 3, and 5) was 9.7, 11.6, and 13.1 times higher respectively, compared to the type-strain. The rate of increase in enzyme activity of ALDH for the three mutant strains (K-2, 3, and 5) was twice as high as that of ADH.

The present inventors named three novel mutant strains (K-2, 3, and 5) adapted to increase aldehyde dehydrogenase (ALDH) activity as PicoYP, PicoYP-01, and PicoYP-02, respectively. The three novel mutant strains were deposited at the Korea Research Institute of Bioscience and Biotechnology's Biological Resources Center and were assigned the deposit numbers of KCTC14983BP, KCTC14984BP, and KCTC14985BP, respectively.

3-3: Content of Coenzyme (NAD and NADP)

NADtotal and NADPtotal in lysates extracted from mutant strains were measured with NADH/NAD+ assay kit and NADPH/NADP+ assay kit, respectively. NAD(P) in the sample was converted to NAD(P)H using NAD(P) cycling buffer and NAD(P) cycling enzyme mix. The chromophoric test reaction was induced with NAD(P) developer measured as absorbance at 450 nm. The chromophoric test reaction was measured as absorbance at 450 nm. The absorbance of the samples was plugged into the equation corresponding to the standard curve, and the NAD(P) total was calculated in the yeast lysate.

The coenzyme content of nine mutant strains (K-1 to K-9) selected in the present invention was measured. The NADtotal of the mutant strains had a minimum of 126 nmole/g and a maximum of 195 nmole/g. The NADtotal of the mutant strain increased at least 7.3 times and up to 10.8 times compared to the type-strain. The NADPtotal content of the mutant strain was a minimum of 2.4 nmole/g and a maximum of 5.8 nmole/g. The NADP total content of the mutant strain increased at least 11.4 times and up to 27.6 times compared to the type-strain.

In the six mutant strains (K-1,4,6,7,8,9), the increase rate of NADPtotal was less than twice the increase rate of NADtotal. The NADPtotal content increase rates of the three novel mutant strains (PicoYP, PicoYP-01, and PicoYP-02) were 25.7, 22.9, and 27.6 times, respectively. The NAD total content increase rates of the three novel mutant strains were 10.8, 9.9, and 11.3 times, respectively. The NADPtotal increase rate of the three novel mutant strains was more than twice the NADtotal increase rate.

3-4: Content of Glutathione (GSH)

The glutathione content of the nine mutant strains was measured in the same manner as Example 1-2. The glutathione content of the mutant strains ranged from a minimum of 0.85% to a maximum of 1.05%. The glutathione content of the mutant strain increased at least 2.7 times and up to 3.3 times compared to the type strain. In three novel mutant strains (PicoYP, PicoYP-01, PicoYP-02), the increase rate of ALDH activity and coenzyme content were higher compared to others.

The three novel mutant yeasts (PicoYP, PicoYP-01, PicoYP-02) had similar glutathione production abilities to the existing deposited strains (Kwon P-1, Kwon P-2, Kwon P-3). The three novel mutant yeasts had significantly increased ADH and ALDH enzyme activities and coenzyme contents compared to the existing deposited strains.

The characteristic and novelty of carbon source preference of strains was analyzed by API 50 CHL kit (API systems, BIOMERIEUX, SA, France).

Preparing the 15 ml of conical tube included 8 ml of YPD medium. Each of the seven mutant strains was inoculated into the prepared conical tube.

After culturing the inoculated conical tubes at 30° C. and 200 rpm for 24 hours, each of the seven mutant strains was secured and extracted from the stage of exponential growth phase. To eliminate the influence of the carbon source contained in the residual YPD medium, the yeast was washed three times using a centrifuge. A yeast suspension of 2McFarland concentration was prepared using API 50 CHL medium. The prepared yeast suspension was filled into the tube of the strip. The strip onto which the suspension was dispensed was cultured at 30° C. for 24 hours.

API 50 CHL medium used for API testing was purple. When acids were produced through energy metabolism, API 50 CHL medium turns blue, green, and finally yellow. In the end, it was recorded which type of carbon source was used

TABLE 3

| Strain | Enzyme activity | | Coenzyme concentration | | GSH | | |
|---|---|---|---|---|---|---|---|
| | ADH | ALDH | $NAD_{total}$ | $NADP_{total}$ | (%) | Name | |
| Type-strain | 74.6 | 2.9 | 17.2 | 0.21 | 0.32 | Reference yeast | KCTC7296 |
| K-1 | 542.26 | 23.11 | 169.8 | 4.1 | 1.00 | KwonP-1 | KCTC13925BP |
| K-2 | 725.11 | 53.1 | 185 | 5.4 | 0.86 | PicoYP | KCTC14983BP |
| K-3 | 866.41 | 67.4 | 171 | 4.8 | 0.85 | PicoYP-01 | KCTC14984BP |
| K-4 | 625.11 | 31.4 | 176 | 5.1 | 0.98 | KwonP-2 | KCTC14122BP |
| K-5 | 975.29 | 72.16 | 195 | 5.8 | 0.89 | PicoYP-02 | KCTC14985BP |
| K-6 | 458.88 | 16.21 | 154 | 3.1 | 1.05 | — | |
| K-7 | 382.69 | 15.23 | 126 | 2.4 | 1.00 | — | |
| K-8 | 422.17 | 16.19 | 142 | 2.9 | 0.99 | — | |
| K-9 | 533.54 | 20.68 | 167 | 3.2 | 1.00 | KwonP-3 | KCTC14123BP |

TABLE 4

| Strain | Enzyme activity | | Coenzyme concentration | | GSH | | |
|---|---|---|---|---|---|---|---|
| | ADH | ALDH | $NAD_{total}$ | $NADP_{total}$ | (%) | Name | |
| Type-strain | 1 | 1 | 1 | 1 | 1 | Reference yeast | KCTC7296 |
| K-1 | 7.3 | 8.0 | 9.9 | 19.5 | 3.1 | KwonP-1 | KCTC13925BP |
| K-2 | 9.7 | 18.3 | 10.8 | 25.7 | 2.7 | PicoYP | KCTC14983BP |
| K-3 | 11.6 | 23.2 | 9.9 | 22.9 | 2.7 | PicoYP-01 | KCTC14984BP |
| K-4 | 8.4 | 10.8 | 10.2 | 17.1 | 3.1 | KwonP-2 | KCTC14122BP |
| K-5 | 13.1 | 24.9 | 11.3 | 27.6 | 2.8 | PicoYP-02 | KCTC14985BP |
| K-6 | 6.2 | 5.6 | 9.0 | 14.8 | 3.3 | — | |
| K-7 | 5.1 | 5.3 | 7.3 | 11.4 | 3.1 | — | |
| K-8 | 5.7 | 5.6 | 8.3 | 13.8 | 3.1 | — | |
| K-9 | 7.2 | 7.1 | 9.7 | 15.2 | 3.1 | KwonP-3 | KCTC14123BP |

[Example 4] Comparison of Carbon Source Preference

It was investigated the carbon source preference for growth of three mutant strains (KwonP-1, KwonP-2, KwonP-3) with high ALDH and glutathione, for which a domestic patent application was filed on Feb. 18, 2020. Various carbon sources used by the reference yeast strain (KCTC7296) for growth were measured. To find the maximum ability of producing ALDH, it was investigated the carbon source preference for growth of three new mutant strains (Pico YP, PicoYP-01, and PicoYP-02).

by mutant strains based on the color change as like: Purple x, Blue+, Green++, and Yellow+++.

All of the seven mutant strains tested used 19 kinds of carbon sources for energy production and growth: L-arabinose, ribose, D-xylose, D-galactose, D-glucose, D-fructose, D-mannose, mannitol, N-acetyl-glucosamine, arbutin, salicin, cellobiose, maltose, lactose, melibiose, sucrose, trehalose, raffinose, gentiobiose.

Rhamnose was used by only three mutant strains: KwonP-1, PicoYP-01, Pico YP-02. Sorbitol was used by four mutant strains: KwonP-1, KwonP-3, PicoYP-01, PicoYP-02. α-methyl-D-mannoside was used by four mutant strains: type strain, KwonP-1, KwonP-2, PicoYP-02. Amygdalin was used by six mutant strains: KwonP-1, KwonP-2, KwonP-3, PicoYP, PicoYP-01, PicoYP-02. D-turanose was used by four mutant strains: type-strain, KwonP-1, KwonP-3, PicoYP-02. D-tagatose was used by three mutant strains: type-strain, KwonP-3, PicoYP-3. Gluconate was used only by type-strain.

Mannitol and sorbitol, which correspond to alcoholic carbon sources, had a significant effect on yeast growth. The three types of novel mutant strains differed from the other four types of yeast in the type of sugar used for growth. The use of the preferred alcoholic carbon source was slightly different between the three new mutant strains (PicoYP, PicoYP-01 and Pico YP-02) [Table 5].

TABLE 5

| | Reference yeast | Kwon P-1 | Kwon P-2 | Kwon P-3 | Pico YP | Pico YP-01 | Pico YP-02 |
|---|---|---|---|---|---|---|---|
| L-Arabinose | ++ | +++ | ++ | +++ | ++ | ++ | +++ |
| Ribose | +++ | +++ | +++ | +++ | +++ | +++ | +++ |
| D-Xylose | + | ++ | + | + | ++ | ++ | + |
| D-Galactose | + | +++ | ++ | ++ | +++ | ++ | ++ |
| D-Glucose | ++ | +++ | +++ | ++ | +++ | ++ | ++ |
| D-Fructose | ++ | +++ | ++ | ++ | +++ | ++ | ++ |
| D-Mannose | ++ | +++ | +++ | ++ | +++ | ++ | ++ |
| Rhamnose | | + | | | | ++ | ++ |
| Mannitol | + | + | + | + | ++ | +++ | +++ |
| Sorbitol | | | + | + | | +++ | +++ |
| α-Methyl-D-Mannoside | +++ | + | + | | | | +++ |
| N-Acetyl-Glucosamine | +++ | +++ | +++ | +++ | +++ | +++ | +++ |
| Amygdalin | | + | + | + | ++ | ++ | ++ |
| Arbutin | +++ | +++ | +++ | +++ | +++ | +++ | +++ |
| Salicin | +++ | +++ | +++ | +++ | +++ | +++ | +++ |
| Cellobiose | +++ | +++ | +++ | +++ | +++ | +++ | +++ |
| Maltose | ++ | +++ | +++ | +++ | +++ | +++ | +++ |
| Lactose | ++ | ++ | ++ | ++ | ++ | ++ | ++ |
| Melibiose | ++ | + | +++ | +++ | ++ | ++ | +++ |
| Sucrose | ++ | +++ | ++ | ++ | +++ | +++ | ++ |
| Trehalose | ++ | + | ++ | ++ | ++ | ++ | ++ |
| Raffinose | ++ | + | + | ++ | ++ | ++ | +++ |
| Gentiobiose | ++ | ++ | ++ | ++ | ++ | ++ | ++ |
| D-Turanose | + | + | | + | | | + |
| D-Tagatose | ++ | | | + | | | ++ |
| Gluconate | + | | | | | | |

[Example 5] Changes in ALDH Activity of Mutant Strains in Gastric Juice

When KARC is administered orally, in order for the enzyme activity to be maintained in the intestine, the enzyme activity must be passed safely without being destroyed by stomach acid, which secretes powerful proteolytic enzymes such as pepsin.

NaOH solution was added to artificial gastric fluid at pH=1.17 to artificially generate two simulated solutions at pH=3 and pH=5, which resemble the human gastric environment during food digestion. 1 g of KARC was added to 7 ml of artificial gastric fluid and 7 ml of two simulated solutions and mixed at 36.5° C. for 5, 30, 60, and 90 min respectively. Afterward NaOH solution was added to reaction mixture to adjust acidity to pH=7, respectively. 10 ml of sample for analysis were taken from the adjusted solution at pH=7, respectively. The activity of ALDH was analyzed from each sample.

Under the condition of pH=1.17, the ALDH activity of the sample decreased by more than 92.88% compared to the control group during 5 minutes of reaction. Under the condition of pH=1.17, the ALDH activity of the sample decreased by an average of 98.89% for 90 minutes. The ALDH activity of the samples decreased by an average of 96.66% over 90 min at pH=3 and 56.83% at pH=5. Ultimately the ALDH activity at pH=3 and 5 remained relatively higher than that at pH=1.17 during the 90-min reaction.

In detail, the ALDH activity of KwonP-1 (KCTC13925BP) at pH=1.17 decreased by 90.94% compared to the control group to 5.57 unit/g when reacted for 5 minutes. The ALDH activity of KwonP-1 decreased by 98.57% to 0.88unit/g for 90 minutes FIG. 17. The enzyme activity at pH=3 and pH=5 remained relatively higher than at pH=1.17. When reacted for 90 minutes, the ALDH activity of KwonP-1 decreased by 96.66% to 5.57 units/g at pH=3, and decreased by 98.57% to 0.88 units/g at pH=5.

The ALDH activity of KwonP-2 (KCTC14122BP) at pH=1.17 decreased by 91.18% to 5.43 unit/g when reacted for 5 minutes. The ALDH activity of KwonP-2 decreased by 98.81% to 0.73 unit/g for 90 minutes FIG. 18. At pH 3 and pH 5, higher enzyme activity was maintained than at pH 1.17. When reacted for 90 minutes, the ALDH activity decreased by 97.62% to 1.47 units/g at pH=3, and decreased by 56.11% to 26.99 units/g at pH=5.

The ALDH activity of KwonP-3 (KCTC14123BP) at pH=1.17 decreased by 89.99% to 6.16 unit/g when reacted for 5 minutes. The ALDH activity of KwonP-3 decreased by 97.85% to 1.32 unit/g for 90 minutes FIG. 19. At pH 3 and pH 5, higher enzyme activity was maintained than at pH 1.17. When reacted for 90 minutes, the ALDH activity decreased by 92.61% to 4.55 units/g at pH=3, and decreased by 62.31% to 22.18 units/g at pH=5.

The ALDH activity of PicoYP (KCTC14983BP) at pH=1.17 decreased by 92.84% to 4.40 unit/g when reacted for 5 minutes. The ALDH activity of PicoYP decreased by 98.33% to 1.03 unit/g for 90 minutes FIG. 20. Higher enzyme activity was maintained at pH 3 and pH 5. When reacted for 90 minutes, the ALDH activity decreased by 96.66% to 2.05 units/g at pH=3, and decreased by 53.97% to 28.31 units/g at pH=5.

The ALDH activity of PicoYP-01 (KCTC14984BP) at pH=1.17 decreased by 95.71% to 2.64 unit/g when reacted for 5 minutes. The ALDH activity of PicoYP-01 decreased by 99.76% to 0.15 unit/g for 90 minutes FIG. 21. At pH 3 and pH 5, higher enzyme activity was maintained than gastric fluid. When reacted for 90 minutes, the ALDH activity decreased by 98.21% to 1.10 units/g at pH=3, and decreased by 58.74% to 25.38 units/g at pH=5.

The ALDH activity of Pico YP-02 (KCTC14985BP) at pH=1.17 decreased by 96.66% to 2.05 unit/g when reacted for 5 minutes. The ALDH activity of Pico YP-02 decreased by 99.76% to 0.15 unit/g for 90 minutes FIG. 22. At pH 3 and pH 5, higher enzyme activity was maintained than in gastric juice. When reacted for 90 minutes, the ALDH activity decreased by 98.21% to 1.10 units/g at pH=3, and decreased by 62.08% to 23.32 units/g at pH=5.

pH 1.17 is the pH of the raw gastric juice secreted. When you eat food, the pH rises from 3 to 5 when raw gastric fluids and food mix in the stomach, so it is unlikely that a pH of 1.17 will be reached. Nevertheless, ALDH activity in the mutant strain was retained even at pH 1.17, which is an extreme condition.

In the end, the ALDH enzyme activity of the novel mutant strains (Pico YP, Pico YP-01, PicoYP-02) was maintained at 2 unit/g to 5 unit/g even though it decreased from 92% to 97% under strongly acidic conditions of pH=1.17. 2-5 units of enzyme activity remain, which is sufficient to function in the intestines. It even remained higher at pH=3 and pH=5 compared to pH=1.17. This was the reason for reaching the conclusion that new mutant strains (Pico YP, PicoYP-01, PicoYP-02) could be administered orally.

[Example 6] Growth Characteristics of 5 L Fermenter Cultures

Each was inoculated into YPD medium (2% peptone, 1% yeast extract, 2% glucose) and primary seed culture was performed at 30° C. and 200 rpm for 18 hours. 20 ml of cultured seed was inoculated into 1980 ml of YPD medium and cultured again in 5 L. Cultivation in a 5 L culture tank was carried out at 30° C. and 200 rpm for 48 hours. Growth curve at OD660 nm and enzyme activity were analyzed using 10 ml of sample collected from secondary culture.

The maximum density (OD660 nm) of KwonP-1 (KCTC13925BP) was 134.4. The maximum density of KwonP-1 was 4.35% higher than that of the type-strain (KCTC7296). The growth curve characteristics and specific growth rate (OD660 nm/hr) of KwonP-1 were similar to those of the type-strain. The ALDH activity of KwonP-1 was 33.6 unit/g. The ALDH activity of KwonP-1 was 11.96 times higher than that of the type-strain FIG. 23.

The maximum density (OD660 nm) of KwonP-2 (KCTC14122BP) was 133.8. The maximum density of KwonP-2 was 3.88% higher than that of the type-strain. The growth of KwonP-2 ended earlier than that of the type-strain. The specific growth rate (OD660 nm/hr) of KwonP-2 was 14.8% higher than that of the type-strain. The ALDH activity of KwonP-2 was 31.5 unit/g. The ALDH activity of KwonP-2 was 11.21 times higher than that of the type-strain FIG. 24.

The maximum density (OD660 nm) of KwonP-3 (KCTC14123BP) was 134.1. The maximum density of KwonP-3 was 4.12% higher than that of the type-strain. The growth of KwonP-3 ended earlier than that of the type-strain. The specific growth rate (OD660 nm/hr) of KwonP-3 was 6.08% higher than that of the type-strain. The ALDH activity of KwonP-3 was 29.5 unit/g. The ALDH activity of KwonP-3 was 10.5 times higher than that of the type-strain FIG. 25.

The maximum density (OD660 nm) of PicoYP (KCTC14983BP) was 123.8. The maximum density of PicoYP was 3.88% higher than that of type-strain. The growth curve characteristics of PicoYP were similar to those of type-strain. The specific growth rate (OD660 nm/hr) of PicoYP was 6.22% higher than that of the type-strain. The ALDH activity of PicoYP was 44.2 unit/g. The ALDH activity of PicoYP was 15.73 times higher than that of the type-strain FIG. 26.

The maximum density (OD660 nm) of PicoYP-01 (KCTC14984BP) was 126.9. The maximum density of PicoYP-01 was 1.47% higher than that of the type-strain. The growth curve characteristics of PicoYP-01 were similar to those of type-strain. The specific growth rate (OD660 nm/hr) of PicoYP-01 was 2.14% higher than that of the type-strain. The ALDH activity of PicoYP-01 was 47.1 unit/g. The ALDH activity of PicoYP-01 was 16.76 times higher than that of the type-strain FIG. 27.

The maximum density (OD660 nm) of PicoYP-02 (KCTC14985BP) was 148.1. The maximum density of PicoYP-02 was 14.99% higher than that of the type-strain. The growth curve of PicoYP-02 was located at the top compared to the type-strain. The specific growth rate (OD660 nm/hr) of PicoYP-02 was 9.64% lower than that of the type-strain. The ALDH activity of PicoYP-02 was 52.68 unit/g. The ALDH activity of PicoYP-02 was 18.75 times higher than that of the type-strain FIG. 28.

[Example 7] Preparation of Mutant Strain Lysates (KARC)

To preserve the enzymes (ALDH, ADH) contained in the mutant enzyme lysate, proteases were removed and inhibited. To preserve the enzymes (ALDH, ADH) contained in the mutant enzyme lysate cell debris was removed. The dried product or lysate of the mutant strain was mixed to prepare the KARC composition.

The mutant strain and the medium in which it was cultured contained various substances, such as yeast metabolites and proteolytic enzymes secreted by yeast. In order to extract and preserve ALDH, coenzyme, and glutathione present in yeast, it is necessary to sufficiently remove substances outside the yeast fungus, and for this purpose, a washing process was performed. Washing of the mutant strain was carried out by dispensing 40 ml of culture medium into 50 ml conical tubes, centrifuging at 13,000 rpm for 15 minutes, and removing the supernatant.

As a result of centrifugation, residual medium remained inside the pellet produced by the yeast bacteria clumping together. After adding 30 ml of purified water, the pellet was sufficiently loosened by vortex, and the previous process was repeated three times to sufficiently remove the remaining medium.

The ethanol resistance of yeast is known to be up to 13%, and yeast bacteria die when exposed to high concentrations of ethanol. The washed pellet was sufficiently dissolved using 10 ml of 20% ethanol solution to induce the death of yeast bacteria. The pellet dissolved in ethanol was stirred at 100 rpm for 30 minutes to proceed with the yeast death process. When the reaction time was completed, 30 ml purified water was added to lower the ethanol concentration to 5%. The previous washing process was repeated three times to sufficiently remove ethanol.

To preserve ALDH and ADH from the decomposition action of proteases present in yeast cells, 10 ml of 1×PBS was prepared by dissolving 2 tablets of protease inhibitor (Pierce protease inhibitor mini tablets, EDTA-free, Thermo Scientific). The above solution was added to the washed yeast pellet and sufficiently released.

To prepare a lysate of the mutant strain prepared in the present invention, 4 g of glass beads were added and stirred to break the yeast cell wall. To prevent denaturation of the enzyme due to the heat generated during the process of crushing the yeast, vortex for 30 seconds and ice incubation for 30 seconds were repeated six times.

After the yeast cell wall disruption was completed, 10 ml of 100 mM potassium phosphate buffer was added and mixed by vortexing for 3-5 seconds. It was centrifuged at 13,000 rpm for 15 minutes to remove cell structures such as yeast cell walls and glass beads. The supernatant was filtered through a 0.2 μm filter (Minisart® Syringe Filter, Sartorius, Goettingen, Germany) to prepare the KARC composition.

To preserve the enzymes (ALDH, ADH) contained in the mutant enzyme lysate, intracellular proteases were removed and inhibited, and cell debris such as cell walls were removed. The KARC composition was prepared with a lysate selected from the 6 mutant strains (KwonP-1, KwonP-2, KwonP-3, PicoYP, PicoYP-01, PicoYP-02), or a mixture thereof in a free ratio [Table 6].

KARC 1 was manufactured from KwonP-1. The enzyme activity of ADH and ALDH of KARC 1 were 461.4 unit/g and 28.6 unit/g, respectively. In KARC 1, the content of coenzymes of NADtotal and NADPtotal were 176.2 nmole/g and 5.1 nmole/g, respectively. The GSH content of KARC 1 was 0.98 wt %.

KARC 2 was manufactured from KwonP-2. the enzyme activity of ADH and ALDH of KARC 2 were 482.1 unit/g and 29.8u nit/g, respectively. In KARC 2, the content of coenzymes of NADtotal and NADPtotal were 175.4 nmole/g and 5.2 nmole/g, respectively. The GSH content of KARC 2 was 0.96 wt %.

KARC 3 was manufactured from KwonP-3. the enzyme activity of ADH and ALDH of KARC 2 were 477.5 unit/g and 28.1 unit/g, respectively. In KARC 3, the content of coenzymes of NADtotal and NADPtotal were 177.2 nmole/g and 5.1 nmole/g, respectively. The GSH content of KARC 3 was 1.00 wt %.

KARC 4 was manufactured from PicoYP. the enzyme activity of ADH and ALDH of KARC 2 were 586.8 unit/g and 33.8 unit/g, respectively. In KARC 4, the content of coenzymes of NADtotal and NADPtotal were 184.3 nmole/g and 5.7 nmole/g, respectively. The GSH content of KARC 4 was 0.84 wt %.

KARC 5 was manufactured from PicoYP-01. the enzyme activity of ADH and ALDH of KARC 5 were 621.6 unit/g and 38.2 unit/g, respectively. In KARC 5, the content of coenzymes of NADtotal and NADPtotal were 186.9 nmole/g and 5.6 nmole/g, respectively. The GSH content of KARC 5 was 0.84 wt %.

KARC 6 was manufactured from PicoYP-02. the enzyme activity of ADH and ALDH of KARC 5 were 664.1 unit/g and 41.6 unit/g, respectively. In KARC 6, the content of coenzymes of NADtotal and NADPtotal were 195.0 nmole/g and 5.8 nmole/g, respectively. The GSH content of KARC 6 was 0.88 wt %.

KARC was manufactured by freely mixing dry powders and lysates prepared from six deposit strains. The average enzyme activities of ADH and ALDH in the composition of KARC were 547.6 unit/g and 33.1 unit/g, respectively. The average contents of coenzyme NADtotal and coenzyme NADPtotal in the composition of KARC were 180.4 nmole/g and 5.4 nmole/g, respectively. The average content of glutathione in the composition of KARC was 0.84 wt %.

The aldehyde decomposition ability of KARC was kept on during the lysate production process. KARC showed the ability to remove endogenous aldehydes such as HNE, MDA, and 3,4-dihydroxyphenyl acetaldehyde (DOPAL).

TABLE 6

| Name | Strain | ADH (Unit/g) | ALDH (Unit/g) | NADtotal (nmole/g) | NADPtotal (nmole/g) | GSH (wt %) |
|---|---|---|---|---|---|---|
| KARC1 | KwonP-1 | 461.4 | 28.6 | 176.2 | 5.1 | 0.98 |
| KARC2 | KwonP-2 | 482.1 | 29.8 | 175.4 | 5.2 | 0.96 |
| KARC3 | KwonP-3 | 477.5 | 28.1 | 177.2 | 5.1 | 1.00 |
| KARC4 | PicoYP | 586.8 | 33.8 | 184.3 | 5.7 | 0.84 |
| KARC5 | PicoYP-01 | 621.6 | 38.2 | 186.9 | 5.6 | 0.83 |
| KARC6 | PicoYP-02 | 664.1 | 41.6 | 195.0 | 5.8 | 0.88 |
| KARC | Average | 547.6 | 33.1 | 180.4 | 5.4 | 0.91 |

[Example 8] Analysis of Sequence of ALDH Contained in the Mutant Strain

It was investigated the differences between both ALD (yeast aldehyde dehydrogenase) of the mutant strains and parent strain. Whole genome sequencing was performed on the parent strain and mutant strains of KwonP-1, KwonP-2, KwonP-3, PicoYP, PicoYP-01, and Pico YP-02. The mutant strain cells were obtained by culturing pure strains on solid medium. The genome sequence of the mutant strain obtained were analyzed.

Among ALDs (yeast aldehyde dehydrogenases) in the novel mutant strains, ALD2 (SEQ ID NO:3) was found to be condensed with ALD3 (SEQ ID NO:4) on chromosome 13. A non-coding region of 689 nucleotides was located between the ALD2 and ALD3 coding genes The ALD2 and ALD3 existed continuously in the same genome. ALD2 and ALD3 encoded respective aldehyde dehydrogenases. ALD2 coding gene was almost similar to ALD3, consist of 1,521 nucleotides and 506 amino acids, but had an 8.2% difference in sequence. ALD2 and ALD3 they were identified as separate aldehyde dehydrogenases that differed from each other in 125 base sequences (8.2%).

In the six mutant strains (KwonP-1, KwonP-2, KwonP-3, PicoYP, PicoYP-01, PicoYP-02), there is no stop codon at the end of the ALD2 sequence, so proteins are synthesized continuously. As a result, a new, larger ALDH enzyme is created by linking a part of ALD2 and ALD3 [SEQ ID NO: 1].

ALD2 [SEQ ID NO. 3] of the type-strain (KCTC7296) consisted of 30 nucleotide sequences (5'-GTTCACAT-AAATCTCTCTTTGGACAACTAA-3') coding 9 amino acids (N-VHINLSLDN-C) at the terminal, excluding the stop codon.

ALD2 of the six mutant strains consisted of specific 42 nucleotide sequences (5'-AGATATAGATTATACACATT-TAGAAAATTAGCCAAAAGAAAA-3') coding 14 amino acids (N-RYRLYTFRKLAKRK-C) between 5'-terminal of ALD2 and ALD3, [SEQ ID NO. 2].

There was no stop codon at the end of the sequence in ALD2 coding gene by deleted from the $1492^{nd}$ nucleotide of ALD2 to $647^{th}$ nucleotide of non-coding region. Finally, the six deposited mutant strains had new mutated gene consist of total 3,054 bases coding novel ALD. [SEQ ID NO: 1].

[Example 9] In Vivo Acetaldehyde (Ach) and Malondialdehyde (MDA) Reduction Effect by Oral Administration of KARC For the acetaldehyde and MDA animal experiments, 5-week-old male Sprague Dawley (SD) rats (Rat) were used. The KARC composition was orally administered to rats at 10 units/kg or 20 units/kg, and alcohol (3 g/kg) was orally administered to the rats 30 minutes after KARC injection.

After the administration was completed, blood samples were collected from the tail vein at 0, 1, 3, 5, and 8 hours after KARC injection, and after centrifugation, plasma was stored at −80° C. FIGS. 1, 2.

9-1: Acetaldehyde Reduction Effect by Oral Administration of KARC

The total acetaldehyde reduction effect by oral administration of KARC was assessed using an Acetaldehyde assay kit (LSBio, Seattle, WA, USA). 20 µl of each sample was dispensed into two wells of a 96 well plate. 80 µl of working reagent (75 µl assay buffer, 8 µl NAD/MTT, 1 µl Enzyme A, 1 µl Enzyme B) was dispensed into one well. In the remaining well, 80 µl of blank working reagent (75 µl assay buffer, 8 µl NAD/MTT, 1 µl Enzyme B) was dispensed. The plate after dispensing was lightly mixed and reacted at room temperature for 30 minutes. When the reaction was completed, the absorbance was measured at 565 nm (520-600 nm).

The concentration of acetaldehyde reached the maximum 1 hour after ethanol administration and showed a tendency to decrease in the KARC composition administration group. In the KARC administration group, acetaldehyde concentration significantly decreased compared to the control group (Vehicle) 1, 3, and 5 hours after ethanol administration. In the KARC high-dose administration group (F), the blood acetaldehyde concentration was 0.356, 0.224, and 0.091 mM, respectively, which decreased by 39.2%, 58.4%, and 72.1% compared to the control group FIG. 1.

9-2: MDA Reduction Effect by Oral Administration of KARC

Total malondialdehyde content in blood was analyzed using the OxiTec™ TBARS assay kit according to the manufacturer's protocol (ZeptoMetric, Buffalo, NY, USA). 100 µl sample, 100 µl 8.1% SDS solution, and 4 ml color indicator (TBA, 10% NaOH solution, 20% acetic acid) were added to the conical tube, and then reacted in a constant temperature water bath at 95° C. for 60 minutes. After completion of the reaction, the sample was centrifuged at 4° C. and 1,600 rpm for 10 minutes and stabilized at room temperature for 30 minutes. 150 µl of supernatant was transferred to a 96 well plate, and absorbance was measured at 530-540 nm.

In the control group (Vehicle), the concentration of MDA in the blood reached the maximum 3 hours after ethanol administration, whereas in the group administered KARC, it reached the maximum value 1 hour after ethanol administration. The concentration of MDA in the blood decreased, showing a significant difference from the control group 3 and 5 hours after ethanol administration. The blood MDA concentration of the KARC high-dose administration group (F) was 0.232 and 0.137 µM, respectively, a decrease of 80.4% and 86.3% compared to the control group FIG. 2.

These results showed that oral administration of KARC was effective in reducing various endogenous aldehydes such as acetaldehyde and malondialdehyde in the blood.

[Example 10] Effect of Reducing Oxidative Stress

Reactive oxygen species or oxidative stress increases when drinking alcohol due to excessive acetaldehyde (Ach) produced by alcohol dehydrogenase (ADH). Aldehyde dehydrogenase (ALDH) acts to convert it into acetic acid and excrete it out of the body. In the case of aldehyde dehydrogenase gene mutation or excessive aldehyde caused by excessive alcohol cause peroxidation of fat.

The resulting acetaldehyde and malondialdehyde worsen oxidative stress and interfere with mitochondrial energy metabolism. Endoplasmic reticulum stress is induced through the accumulation of denatured proteins in cells, leading to cell death.

The concentration of blood acetaldehyde was measured over time following alcohol consumption FIG. 3. The area under the curve (AUC) of blood acetaldehyde (Ach) was 13.02±1.18 mg·h/dL for alcohol consumption alone. When administered at a dose of KARC 10 units/kg, the area under the curve (AUC) of blood acetaldehyde (Ach) significantly decreased by 26.13% compared to alcohol consumption alone, measuring 9.39±1.07 mg·h/dL (P=0.005).

At a dose of KARC 20 units/kg administration, the AUC of blood acetaldehyde (Ach) decreased significantly by 55.71% compared to alcohol consumption alone, measuring 5.22±0.99 mg·h/dL (P<0.001). When comparing the KARC 10 units/kg administration group with the KARC 20 units/kg administration group, the blood acetaldehyde (Ach) in the KARC 20 units/kg group decreased significantly (P=0.034). KARC demonstrated dose-dependent reduction in the total amount of blood acetaldehyde (Ach) over time.

The reduction in blood acetaldehyde (Ach) concentration due to KARC administration has a positive impact on reducing oxidative stress and promoting health.

The concentration of blood malondialdehyde (MDA) was measured during the chemotherapy period FIG. 4. The concentration of blood MDA in the control group was 0.607±0.161 µM. The group undergoing treatment with KARC showed a significant 63.3% reduction in blood MDA concentration, measuring 0.223±0.033 µM compared to the control group (P<0.001).

In the control group, the blood MDA concentration ranged from 0.427 µM to 0.885 µM with a substantial variability. In the KARC administration group, the range was significantly reduced, with values ranging from 0.158 µM to 0.269 µM. This not only confirmed the effect of reducing blood MDA concentration but also stabilizing it, as demonstrated in FIG. 5.

Various factors, such as drug intake, stress, and intense physical exercise, lead to an increase in intracellular reactive oxygen species. This triggers lipid peroxidation reactions and oxidative processes in endogenous amines such as dopamine, norepinephrine, serotonin, histamine, and more. Reactive aldehyde compounds, including 4-hydroxynonenal (HNE), malondialdehyde (MDA), acetaldehyde (Ach), and dopamine-induced aldehyde, accumulate within cells, exacerbating oxidative stress.

These aldehydes subsequently react with surrounding proteins and undergo secondary metabolic processes to form stable end products such as Malondialdehyde-acetaldehyde adduct (MAA) and Malondialdehyde lysine adducts (M-lys adducts), known as Advanced Lipid Peroxidation End Products. The accumulation of these products exerts toxic effects on various cells, further intensifying oxidative stress.

This cumulative oxidative stress disrupts mitochondrial energy metabolism within cells and leads to the buildup of aldehyde intermediates in aldehyde-based sugar metabolism, including methylglyoxal (MG) and glyceraldehyde-3-phosphate (GA3P). The chain reaction involving aldehydes results in the accumulation of stable final glycoxidation products known as advanced glycation end products (AGEs), which weaken intracellular antioxidant defense systems like glutathione (GSH). These processes elevate endoplasmic reticulum (ER) stress, leading to increased cellular apoptosis in nerve cells.

The increase in reactive oxygen species and oxidative stress is associated with elevated levels of reactive aldehydes like HNE and MDA, as well as modified proteins such as advanced glycation end products (AGEs) and advanced lipid peroxidation end products (ALEs). This cascade of events is known to involve mutual reinforcement and amplification, leading to heightened endoplasmic reticulum stress (ER stress).

[Example 11] Acute Oral Administration Test 11-1. Preparation of Experimental Animals The experimental animals were female and male ICR mice (7 weeks old). The received ICR mice were acclimatized for 7 days. The general symptoms of the adopted mice were observed during the acclimatization period, and only healthy animals were used for short-term administration toxicity tests. Feed and water were consumed ad libitum. Based on the average body weight of about 20 g the day before oral administration, groups were separated into 10 groups, 5 for each group, and 5 for each group.

11-2. Administration of Test Substances

The test substance was prepared by dissolving it in physiological saline so that the dosage for experimental animals was 0, 750, 3,000, and 5,000 mg/kg, respectively, based on the content of the mutant yeast lysate KARC of the present invention.

The standards for administered dosage were in accordance with the Ministry of Food and Drug Safety's Korea national Toxicology Program (KNTP) toxicity test manual. The maximum application dose of 5,000 mg/kg guided by the KNTP manual was set as the maximum concentration for this experiment. The samples prepared for each group were orally administered once to each test animal. For the normal group (G1), physiological saline was administered.

11-3. Observation and Autopsy

For animals in all test groups, symptoms of mice were observed at least once a day from the date of acquisition to the date of necropsy. Symptoms were observed for 7 days after oral administration. After observing the rat's symptoms, an autopsy was performed. During the autopsy of the rat, changes in each organ were observed with the naked eye.

A single-dose toxicity test of the ALDH-containing KARC composition of the present invention was conducted using mice. As a result, no cases of mouse death were observed for 7 days at concentrations of the mutant yeast KARC up to 5,000 mg/kg. No unusual features, such as weight gain or changes in feed intake, were found in the mice. No unusual findings were found in the autopsy results conducted after the end of observation.

[Example 12] The Effect of Oral Administration of KARC for Alleviation of Memory Impairment and Abnormal Amyloid Protein 5×FAD mice model was created to confirm the effects of KARC on memory impairment and cognitive function improvement, as well as to verify the reduction in abnormal amyloid beta protein deposition. The administration of KARC improved behavior of 5×FAD mouse in the Y-maze behavioral test to assess memory, and reduced inflammatory cells and amyloid plaques in brain tissue.

12-1: Preparation of 5×FAD Mouse Model and Administration of KARC

5×FAD mice expresses three human APPs [Swedish (K670N/M671L), Florida (I716V), and London (V7171)] and two PSENIs (M146L and L286V). Total five mutations in 5×FAD mice are closely related with Alzheimer's disease.

The expression of these two genes is regulated by neural-specific elements of the mouse Thy1 promoter to induce overexpression in the brain. Mice in the 6799 line have the highest expression of amyloid beta precursor protein (APP), which is associated with the rapid accumulation of the 42 amino acids of beta amyloid.

5×FAD mice accumulate amyloid plaques from 1.5 months of age, accompanied by gliosis, which is found in mice around 2 months of age. Amyloid pathology is more severe in females than in males. Female mice are primarily used, and neuronal loss occurs in multiple brain regions, starting at approximately 6 months of age in areas with amyloidosis, where neuron loss is most prominent. Mice develop Alzheimer's disease with a variety of cognitive impairment and motor disorder.

After cutting off the tails of mice born through double mating and confirming the expression of APP and PSEN1 through GENOMIC DNA PCR, 5×FAD mice expressing both genes were selected for the experiment.

17-month-old Alzheimer's model mice selected from 5×FAD female mice and non-transgenic (Ntg) mice were divided into 4 groups (n=5/group). In the control group, only PBS was administered to Ntg mice every day for one month. In the Vehicle group, to 5×FAD mice.

Ntg or 5×FAD mice was orally administered PBS with KARC (20 units/kg/day) under the same conditions, respectively FIG. 6.

12-2: The Result of Behavioral Test and Memory Assessment by the Oral Administration of KARC The Y-maze test was performed to assess short-term memory in 5×FAD mice, a model of Alzheimer's disease. Rodents typically prefer to investigate a new arm of the maze rather than returning to one that was previously visited. Many parts of the brain including the hippocampus, septum, basal forebrain, and prefrontal cortex are involved in this task.

Testing occurred in a Y-shaped maze with three plastic arms at a 120° angle from each other. The mice were allowed to freely explore three mazes from the central hub of the maze. The ratio, expressed as a percentage, was calculated based on the number of times the mice visited new locations compared to the total number of visits.

Cognitive impairment was observed as Alzheimer's progressed. In 5×FAD mice, an Alzheimer's model, the rate of visiting a new place of maze using the Y-maze test decreased to 47.4%. In mice administered KARC, it increased to 65.02%. This suggests that KARC has the potential as a treatment for improving memory impairment caused by Alzheimer's disease and restoring cognitive function due to Alzheimer's dementia FIG. 7.

12-3-1: Preparing Brain Tissue

Mice were anesthetized by injecting chloral hydrate (40 mg/kg, i.p), transcardially perfused with a saline solution containing 0.5% sodium nitrate and heparin (10 U/ml). Brain tissue was fixed with 4% paraformaldehyde dissolved in 0.1 M phosphate buffer (PB, pH 7.2).

Whole-brain tissues were dissected from the skull, post-fixed overnight with 4% paraformaldehyde in 0.1 M PB at 4° C. Stored in 30% sucrose solution in 0.05 M PBS at 4° C. until they sank.

The brains were frozen-sectioned on a Cryostat (Microsystems A G, Leica, Wetzlar, Germany) in 30 μm thick coronal sections. The brains stored in a cryoprotectant (25% ethylene glycol, 25% glycerol, 0.2 M PB, and water) at 4° C. until use. Hippocampus sections were changes in the brain were observed through immunostaining.

12-3-2: Immunohistochemical Staining

Thioflavin S (Sigma-Aldrich, St. Louis, MO, USA) was used to stain abnormally aggregated amyloid plaques in brain sections (30 μm) containing the hippocampus of 5×FAD mice, an Alzheimer's model. Thioflavin S is used for histological staining and biophysical research to visualize protein aggregates such as amyloid plaques. A 1% Thioflavin S solution was prepared by dissolving Thioflavin S in distilled water, followed by filtration through a 0.45 μm filter. Brain tissue, including the hippocampus, was stained with the 1% Thioflavin S solution for 5 minutes, washed three times with PBS, cover-slipped, and analyzed using a fluorescent microscope (Fluorescent Microscopy) FIG. 8.

Astrocytes from brain sections (30 μm thickness) containing hippocampus, a neuroinflammatory cell, were incubated with the rabbit anti-glial fibrillary acidic protein (anti-GFAP, 1:5000; Neuromics, Edina, MN, USA) or with rabbit anti-ionized calcium binding adaptor molecule 1 (anti-Iba-1, 1:1000; Wako, Osaka, Japan), respectively.

The incubated astrocytes was stained with biotinylated an-ti-rabbit IgG, or with an avidin-biotin peroxidase complex (ABC) standard kit (Vector Laboratories, Burlingame, CA, USA), respectively.

Signals were detected after incubating the stained sections with 0.5 mg/ml 3,3'-diaminobenzidine (Sigma, St. Louis, MO, USA) in 0.1 M PBS containing 0.003% $H_2O_2$. To quantify GFAP or Iba-1 positive cells respectively, the image of stained brain sections were analyzed under a bright-field microscope (Olympus Optical, Tokyo, Japan).

12-3-3: The Method of Intensity and Counting of Amyloid Plaques

The fluorescence intensity and total number of amyloid plaques were measured in the hippocampus of 5×FAD mice, an Alzheimer's model. Fluorescence intensity and total count of amyloid plaques stained in the hippocampus were analyzed using Image J software (National Institutes of Health, Bethesda, MD, USA) on images captured at a 40× magnification.

12-4: Changes in Brain Substances Caused by Oral Administration of KARC in 5×FAD Mice, An Alzheimer's Model 12-4-1: Effect of KARC on Amyloid Plaque Reduction in Whole Brain of Alzheimer's Model To measure abnormally aggregated amyloid protein in 5×FAD mice, an Alzheimer's model, amyloid plaques in brain tissues including hippocampus were stained by white Thioflavin S. Amyloid plaques were collections of misfolded proteins, consisted of a mixture of degenerated neurons and beta-amyloid aggregates. These plaques gradually accumulate in the brain as they cannot be broken down or removed. The accumulation of these amyloid plaques in specific organs or tissues, leading to functional impairment and deterioration, is known as amyloidosis. When amyloid plaques deposit in brain neurons, they trigger various neurodegenerative diseases. Abnormally structured proteins, such as amyloid plaques, play a central role in Alzheimer's disease.

In 17-month-old female non-transgenic (Ntg) mice, similar to normal mice, no amyloid plaques were observed in the brain. In 17-month-old female 5×FAD mice (vehicle group), amyloid plaques were observed to accumulate throughout the brain, including the hippocampus. In 5×FAD mice orally administered KARC (20 units/kg/day), amyloid plaques were overall reduced compared to the vehicle group FIG. 8.

The Image J program was used to quantify the intensity and number of amyloid plaques accumulated in the hippocampus of the brain.

No amyloid plaques were observed in 17-month-old female Ntg mice in control group, and the intensities of amyloid plaques were 11.47 in the vehicle group and 12.37 in the KARC-administered group, showing no significance comparative to control group. The intensity of amyloid plaques in 17-month-old female 5×FAD mice was 52.36 in vehicle group and 34.76 in the KARC-administered group, significantly decreased by 66.38% compared to the vehicle group (p<0.001) FIG. 9.

In the quantifying number of amyloid plaques, there was no pathologically difference, 319 amyloid plaques in 17-month-old female non-transgenic mice (control group) and 501 in the KARC administration group. In the number of amyloid plaques using 17-month-old female 5×FAD mice, it was significantly reduced 2272 by 70.09% in the KARC-administered group (p<0.001) compared to 3202 in the vehicle group. FIG. 10.

12-4-2: The Reduction of Neuronal Inflammation in Microglia and Astrocyte by Oral Administration of KARC in 5×FAD Mice, an Alzheimer's Disease Model The efficacy of KARC in alleviating neuroinflammation in the 5×FAD mice model was assessed by staining microglia and astrocyte. The hippocampus in brain tissue was immune-stained by using Iba-1 (microglia) antibody FIG. 11 and GFAP (astrocyte) antibody FIG. 14 and then analyzed.

In 17-month-old non-transgenic (Ntg) mice, the CA1 and CA3 regions of the hippocampus was found that both microglial and astrocytic cells were in a resting state. In regions of CA1 and CA3 in hippocampus of 17-month-old 5×FAD mice, the cells of microglia and astrocyte were morphologically enlarged by activation. And neurites became brighter and longer by dendritic process. the reason was that brain neuroinflammation was induced by the accumulation of abnormal amyloid plaques.

Neuroinflammatory activation of hippocampal microglia and astrocytes was suppressed in 5×FAD mice orally administered KARC (20 units/kg/day) FIGS. 11, 14.

In 17-month-old 5×FAD mice, the number of microglia with positively activated Iba-1 was 125±45 in the CA1 region and 118±14 in the CA3 region. In the hippocampus of 17-month-old 5×FAD mice administered KARC orally, the number of Iba-1 positively activated microglia decreased to 59±11 in the CA1 region and 80±12 in the CA3 region FIGS. 12, 13.

In the hippocampus of 17-month-old 5×FADmice, the number of GFAP positively activated astrocyte was 137±1 in the CA1 region and 114±17 in the CA3 region. In the hippocampus of 17-month-old 5×FADmice administered KARC orally, the number of GFAP positively activated astrocyte decreased to 90±9 in the CA1 region and 87±5 in the CA3 region FIGS. 15, 16. It was confirmed that oral administration of KARC suppressed the neuroinflammatory activation of hippocampal microglia and astrocytes through quantification of activated cells.

It is well-documented that neuroinflammation plays a crucial role in inducing various pathological features observed in Alzheimer's disease. The sustained activation of microglia and other immune cells in the brain has been shown to exacerbate both amyloid and tau pathology, potentially serving as a link to the onset of the disease.

Cytokines, such as IL-1 and IL-6, which mediate inflammatory responses, have been shown to accumulate the amount of amyloid-beta or induce hyperphosphorylation of tau proteins, as well as trigger chronic inflammatory processes in microglia and astrocyte. This indicates that inflammatory responses may directly contribute to the pathological manifestation of Alzheimer's disease.

Iba-1 (ionized calcium-binding adapter molecule 1) is one of subtypes of allograft inflammatory factor-1 (AIF-1). Iba-1 is a protein specifically expressed in microglia of the immune cells and the central nervous system. Iba-1 is overexpressed in microglia in response to nerve injury as like central nervous system ischemia and various other brain disorders.

The reduction of Iba-1 expression by KARC administration signifies its potential for reducing brain nerve damage and improving ischemia in central nervous system, and suggests the possibility of ameliorating various brain disorders.

GFAP (glial fibrillary acidic protein) is a fibrous acidic protein present in brain nerve cells. GFAP is a marker for astrocytes, which are distributed in the central nervous system (CNS). GFAP plays a crucial role in regulating the motility and morphology maintenance of astrocytes by contributing to myelin formation in nerve cells.

In mammals, GFAP expression in astrocytes is also known to be specifically increased in the brain damaged by a variety of causes, both physical and chemical. The increase of abnormal astrocyte in damaged brain leads to neurodegenerative diseases through increased inflammation and induced death of brain nerve cells, and accelerate the disease progression.

The decrease in abnormal GFAP indicates that astrocyte damages were restored by KARC administration, which may be effective in preventing and ameliorating neurodegenerative diseases.

The treatment with KARC significantly suppressed the neuroinflammatory response in 5×FAD mice as analyzed by the degree of activation in microglial and astrocyte. These data indicate that KARC has therapeutic effects on neuroinflammation in vivo.

In conclusion, KARC has a significant impact on improving memory and cognitive function in 5×FAD mice, alleviating brain inflammation, and regulating down the abnormal accumulation of amyloid plaques. This research indicates that KARC could be an effective treatment for dementia.

[Example 13] Examples of Manufacturing Food and Pharmaceutical Compositions for Memory Impairment and Cognitive Function by Reducing Amyloid Beta Plague and Endogenous Acetaldehydes Food and pharmaceutical compositions containing KARC as an active ingredient for improving memory impairment and cognitive function were prepared. It is possible to prepare food or pharmaceutical compositions of various composition ratios containing KARC powder. As an example, the powder composition according to the present invention has the function of improving memory impairment and cognitive function through ingestion of 13 g of the composition twice a day. The weight ratio between the components and phases of the food or pharmaceutical composition containing the powder composition is shown in [Table 7].

TABLE 7

| | Ingredient | Ratio (wt %) |
|---|---|---|
| A composition for improving memory and cognitive function | KARC dry powder | 50 |
| | Fructo-oligosaccharides | 9 |
| | Stevia | 5 |
| | Citric acid anhydrous | 10 |
| | Iso-malto | 4.3 |
| | Xylitol | 2.5 |
| | Citrus juice Powder | 6.2 |
| | Citrus Flavors Powder | 13 |

INDUSTRIAL APPLICABILITY

In the food and pharmaceutical composition, KARC dry powder, excipients, and natural sweeteners such as fructo-oligosaccharides, enzyme-treated stevia (Stevia), anhydrous citric acid, iso-maltodextrins (Iso-malto), and xylitol, citrus juice powder, and citrus flavor powder were added. Processing and testing of raw materials and final products of food or pharmaceutical compositions were conducted in accordance with the general test methods and the Health Functional Foods Act described in the Korean Food Code.

KARC-containing foods or pharmaceutical compositions can prevent or improve cognitive function deterioration.

Through the above examples, the mutant yeast composition KARC containing aldehyde dehydrogenase was described in detail: pharmacological effects on Alzheimer's treatment or Lewy body dementia phenomenon, administration methods, therapeutically effective doses for disease models, acute oral administration toxicity, and representative examples of food or pharmaceutical compositions. Although the efficacy of KARC has been described in detail through the above examples, these are only examples of the present invention.

A person skilled in the art can easily derive various modifications and other embodiments equivalent to the present invention from the above-described embodiments of the present invention.

Even foods or therapeutic agents containing a modified form of aldehyde dehydrogenase that embodies the technical gist of the present invention described in the patent claims fall within the scope of legal protection of the present invention.

The invention claimed is:

1. A method for treating Alzheimer Dementia in a subject in need thereof, comprising administering to the subject a food composition containing aldehyde dehydrogenase, wherein the aldehyde dehydrogenase is encoded by a gene having the sequence of SEQ ID NO: 1.

2. The method for treating Alzheimer Dementia according to claim 1, wherein the aldehyde dehydrogenase dehydrogenates an endogenous aldehyde.

3. The method for treating Alzheimer Dementia according to claim 2, wherein the endogenous aldehyde is produced by the oxidation of alcohol or an endogenous amine compound.

4. The method for treating Alzheimer Dementia according to claim 3, wherein the endogenous amine compound is selected from the group consisting of: dopamine, norepinephrine, serotonin, and gamma-aminobutyric acid (GABA).

5. The method for treating Alzheimer Dementia according to claim 2, wherein the endogenous aldehyde is selected from the group consisting of: formaldehyde, acetaldehyde, 4-hydroxy-2-nonenal, non-2-enal, 4-hydroxy-hexanal, 4-oxo-nonena, malondialdehyde (MDA), propionaldehyde, hexanal-(hexanal), palmitic aldehyde, succinic aldehyde and acrylic aldehyde.

6. The method for treating Alzheimer Dementia according to claim 1, wherein the aldehyde dehydrogenase is contained in lysate of any one or a mixture thereof selected from the group consisting of: *Saccharomyces cerevisiae* KCTC13925BP, *Saccharomyces cerevisiae* KCTC14122BP, *Saccharomyces cerevisiae* KCTC14123BP, *Saccharomyces cerevisiae* KCTC14983BP, *Saccharomyces cerevisiae* KCTC14984BP and *Saccharomyces cerevisiae* KCTC14985BP.

* * * * *